(12) United States Patent
Skelton et al.

(10) Patent No.: US 8,219,206 B2
(45) Date of Patent: Jul. 10, 2012

(54) DWELL TIME ADJUSTMENTS FOR POSTURE STATE-RESPONSIVE THERAPY

(75) Inventors: Dennis M. Skelton, Bloomington, MN (US); Jon P. Davis, St. Michael, MN (US)

(73) Assignee: Medtronic, Inc., Minneapolis, MN (US)

( * ) Notice: Subject to any disclaimer, the term of this patent is extended or adjusted under 35 U.S.C. 154(b) by 487 days.

(21) Appl. No.: 12/433,815

(22) Filed: Apr. 30, 2009

(65) Prior Publication Data

US 2010/0010390 A1    Jan. 14, 2010

Related U.S. Application Data

(60) Provisional application No. 61/080,049, filed on Jul. 11, 2008.

(51) Int. Cl.
*A61N 1/00* (2006.01)
(52) U.S. Cl. .................. 607/62; 607/17; 607/30
(58) Field of Classification Search .............. 607/17, 607/30, 62; 600/480, 529, 544, 546
See application file for complete search history.

(56) References Cited

U.S. PATENT DOCUMENTS

| | | | |
|---|---|---|---|
| 4,297,685 A | 10/1981 | Brainard, II | |
| 4,365,633 A | 12/1982 | Loughman | |
| 4,543,955 A | 10/1985 | Schroeppel | |
| 4,550,736 A | 11/1985 | Broughton et al. | |
| 4,566,456 A | 1/1986 | Koning et al. | |
| 4,771,780 A | 9/1988 | Sholder | |
| 4,776,345 A | 10/1988 | Cohen et al. | |
| 4,846,180 A | 7/1989 | Buffet | |
| 4,846,195 A | 7/1989 | Alt | |
| 5,031,618 A | 7/1991 | Mullett | |

(Continued)

FOREIGN PATENT DOCUMENTS

DE    19831109    1/2000

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Niketa Patel
*Assistant Examiner* — Mallika Fairchild
(74) *Attorney, Agent, or Firm* — Shumaker & Sieffert, PA

(57) ABSTRACT

A medical device detects a patient posture state and adjusts therapy based on the detected posture state. A patient posture state may be transient. To avoid adjusting therapy in response to transient posture states, a dwell time may be imposed. Using the dwell time, only those posture states that are assumed by a patient for a minimum length of time will result in therapy adjustment. To help ensure that the dwell time is set to an appropriate length of time, patient therapy adjustment data may be analyzed. Therapy adjustments made during the dwell time may indicate that the dwell time is too long. Therapy adjustments made prior to the initiation of the dwell time may also indicate that the dwell time is too long. Therapy adjustments made by the patient after expiration of the dwell time may indicate that the dwell time is too short. Based on analysis of the therapy adjustment data, the dwell time can be adjusted to a length that is appropriate for the patient and/or posture state.

45 Claims, 22 Drawing Sheets

U.S. PATENT DOCUMENTS

| | | | |
|---|---|---|---|
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 * | 10/2002 | Pianca et al. ..................... 607/18 |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 * | 12/2006 | Koh et al. ..................... 607/19 |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al. |
| 7,214,197 B2 | 5/2007 | Prass |
| 7,218,964 B2 | 5/2007 | Hill et al. |

| Patent/Pub No. | Date | Name |
|---|---|---|
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Miesel et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0156504 A1 | 10/2002 | Chen et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247724 A1 | 11/2006 | Gerber et al. |
| 2006/0247732 A1 | 11/2006 | Wesselink |
| 2006/0247739 A1 | 11/2006 | Wahlstrand et al. |
| 2006/0253174 A1 | 11/2006 | King |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1* | 6/2007 | Bourget et al. .................. 607/62 |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1* | 10/2007 | Miesel et al. .................. 600/595 |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |

| | | | |
|---|---|---|---|
| 2008/0204255 A1 | 8/2008 | Flexer et al. | |
| 2008/0269812 A1 | 10/2008 | Gerber et al. | |
| 2008/0269843 A1 | 10/2008 | Gerber | |
| 2008/0281376 A1 | 11/2008 | Gerber et al. | |
| 2008/0281379 A1 | 11/2008 | Wesselink | |
| 2008/0281381 A1 | 11/2008 | Gerber et al. | |
| 2008/0288200 A1 | 11/2008 | Noble | |
| 2008/0300449 A1 | 12/2008 | Gerber et al. | |
| 2008/0300470 A1 | 12/2008 | Gerber et al. | |
| 2009/0030263 A1 | 1/2009 | Heruth et al. | |
| 2009/0036951 A1 | 2/2009 | Heruth et al. | |
| 2009/0046056 A1 | 2/2009 | Rosenberg et al. | |
| 2009/0076343 A1 | 3/2009 | James et al. | |
| 2009/0082829 A1 | 3/2009 | Panken et al. | |
| 2009/0099627 A1 | 4/2009 | Molnar et al. | |
| 2009/0105785 A1 | 4/2009 | Wei et al. | |
| 2009/0118599 A1 | 5/2009 | Heruth et al. | |
| 2009/0228841 A1 | 9/2009 | Hildreth | |
| 2009/0233770 A1 | 9/2009 | Vincent et al. | |
| 2009/0259216 A1 | 10/2009 | Drew et al. | |
| 2009/0264789 A1 | 10/2009 | Molnar et al. | |
| 2009/0306740 A1 | 12/2009 | Heruth et al. | |
| 2010/0010380 A1 | 1/2010 | Panken et al. | |
| 2010/0010381 A1 | 1/2010 | Skelton et al. | |
| 2010/0010382 A1 | 1/2010 | Panken et al. | |
| 2010/0010383 A1 | 1/2010 | Skelton et al. | |
| 2010/0010384 A1 | 1/2010 | Panken et al. | |
| 2010/0010385 A1 | 1/2010 | Skelton et al. | |
| 2010/0010386 A1 | 1/2010 | Skelton et al. | |
| 2010/0010387 A1 | 1/2010 | Skelton et al. | |
| 2010/0010388 A1 | 1/2010 | Panken et al. | |
| 2010/0010389 A1 | 1/2010 | Davis et al. | |
| 2010/0010391 A1 | 1/2010 | Skelton et al. | |
| 2010/0010392 A1 | 1/2010 | Skelton et al. | |
| 2010/0010432 A1 | 1/2010 | Skelton et al. | |
| 2010/0010571 A1 | 1/2010 | Skelton et al. | |
| 2010/0010572 A1 | 1/2010 | Skelton et al. | |
| 2010/0010573 A1 | 1/2010 | Skelton et al. | |
| 2010/0010574 A1 | 1/2010 | Skelton et al. | |
| 2010/0010575 A1 | 1/2010 | Skelton et al. | |
| 2010/0010576 A1 | 1/2010 | Skelton et al. | |
| 2010/0010577 A1 | 1/2010 | Skelton et al. | |
| 2010/0010578 A1 | 1/2010 | Skelton et al. | |
| 2010/0010579 A1 | 1/2010 | Skelton et al. | |
| 2010/0010580 A1 | 1/2010 | Skelton et al. | |
| 2010/0010583 A1 | 1/2010 | Panken et al. | |
| 2010/0010584 A1 | 1/2010 | Skelton et al. | |
| 2010/0010585 A1 | 1/2010 | Davis et al. | |
| 2010/0010586 A1 | 1/2010 | Skelton et al. | |
| 2010/0010587 A1 | 1/2010 | Skelton et al. | |
| 2010/0010588 A1 | 1/2010 | Skelton et al. | |
| 2010/0010589 A1 | 1/2010 | Skelton et al. | |
| 2010/0010590 A1 | 1/2010 | Skelton et al. | |
| 2010/0030286 A1 | 2/2010 | Goetz et al. | |
| 2010/0121415 A1 | 5/2010 | Skelton et al. | |
| 2010/0174155 A1 | 7/2010 | Heruth et al. | |

FOREIGN PATENT DOCUMENTS

| | | |
|---|---|---|
| DE | 10024103 | 11/2001 |
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universität Freiburg, Germany, Mar. 2000, 28 pp.

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.

Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.

Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.

Goodrich et al., "The Prediction of Pain Using Measures of Sleep Quality," Pain Digest, 8:23-25, 1998.

Heinz et al., "Using Wearable Sensors for Real-time Recognition Tasks in Games of Martial Arts— An Initial Experiment," Institute for Computer Systems and Networks (CSN), UMIT- University of Health Systems, Medical Informatics and Technology Hall in Tyrol, Austria, 2006, 5 pp., http://eis.comp.lancs.ac.uk/fileadmin/relate/publication/2006-WearableSensors.pdf.

Hendelman et al., "Validity of Accelerometry for the Assessment of Moderate Intensity Physical Activity in the Field," Medicine & Science in Sports & Exercise, pp. S442-S449, 2000.

Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.

Husak, "Model of Tilt Sensor Systems, "ICECS 2002, $9^{th}$ IEEE International Conference on Electronics, Circuits and Systems, vol. 1, pp. 227-230, 2002.

Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.

Kassam, "2005 EDP Topic "MK4": Tremor Data-Logger for Parkinson's Disease Patients," http://www.ee.ryerson.ca/~courses/edp2005/MK4.html, 3 pp., 2005.

Kerr et al., "Analysis of the sit-stand-sit movement cycle in normal subjects," Clinical Biomechanics, vol. 12, No. 4, pp. 236-245, 1977.

Kiani et al., "Computerized Analysis of Daily Life Motor Activity for Ambulatory Monitoring," Technology and Health Care 5, pp. 307-318, 1997.

Kitchin et al., "Compensating for the 0 g Offset Drift of the ADXL50 Accelerometer," Analog Devices Application Note AN-380, 2 pp.

Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.

Leiper et al., "Sensory Feedback for Head Control in Cerebral Palsy," Physical Therapy, vol. 61, No. 4, pp. 512-518, Apr. 1981.

Lorussi, "Wearable, Redundant Fabric-Based Sensor Arrays for Reconstruction of Body Segment Posture," IEEE Sensors Journal, vol. 4, No. 6, pp. 808-817, Dec. 2004.

Mathie et al., "A Pilot Study of Long-Term Monitoring of Human Movements in the Home Using Accelerometer," Journal of Telemedicine and Telecare10:144-151, Jun. 2007.

Mathie et al., "Determining Activity Using a Triaxial Accelerometer," Proceedings of the Second Joint EMBS/BMES Conference, Houston, TX, pp. 2481-2482, Oct. 23-26, 2002.

Mattmann et al., "Recognizing Upper Body Postures Using Textile Strain Sensors," Proceedings Eleventh IEEE International Symposium on Wearable Computers, ISWC, pp. 29-36, 2007.

Mendez et al., "Interactions Between Sleep and Epilepsy," Journal of Clinical Neurophysiology, American Clinical Neurophysiology Society, 18(2), pp. 106-127, 2001.

Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.

Slyper et al., "Action Capture with Accelerometers," Eurographics/ACM SIGGRAPH Symposium on Computer Animation, Carnegie Mellon University, 7 pp., 2008.

Smith et al., "How do sleep disturbance and chronic pain inter-relate? Insights from the longitudinal and cognitive-behavioral clinical trials literature," Sleep Medicine Reviews, YSMRV 286, pp. 1-14, 2003.

Smith et al., "Presleep cognitions in Patients with Insomnia Secondary to Chronic Pain," Journal of Behavioral Medicine, vol. 24, No. 1, pp. 93-114, 2001.

Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.

Trolier-Mckinstry et al., "Thin Film Piezoelectrics for MEMS," Journal of Electroceramics, v. 12, No. 1-2, pp. 7-17, Jan./Mar. 2004.

Tuck, "Implementing Auto-Zero Calibration Technique for Accelerometers," Freescale Semiconductor Application Note AN3447, 5 pp., Mar. 2007.

Tuisku, "Motor Activity Measured by Actometry in Neuropsychiatric Disorders," Department of Psychiatry, University of Helsinki, Helsinki, Finland, 115 pp., 2002.

Vega-Gonzalez, "Upper Limb Activity Monitoring," Arch Phys Med Rehabil, vol. 86, pp. 541-548, Mar. 2005.

Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.

PCT/US09/49184: International Search Report and Written Opinion dated Apr. 7, 2009, 16 pp.

U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

* cited by examiner

DWELL TIME ADJUSTMENTS FOR POSTURE STATE-RESPONSIVE THERAPY

This application claims the benefit of U.S. Provisional Application Ser. No. 61/080,049, filed Jul. 11, 2008, entitled "Posture State Detection System and Method", which is herein incorporated by reference in its entirety.

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient may be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure is directed to posture-responsive therapy. An implantable medical device (IMD) detects a posture state of the patient and adjusts therapy according to the detected posture state. A posture state may refer to a patient posture or a combination of patient posture and patient activity. As patient posture state changes, therapy may be adjusted. For example, the therapy may be adjusted to accommodate differences in a patient's response to therapy when the patient occupies different posture states. Upon detection of a change in posture state, the IMD may adjust therapy delivered to the patient.

A patient posture state may be transient, i.e., brief or temporary. To avoid adjusting therapy in response to transient posture states, a time delay may be imposed. The time delay, which may be referred to as a dwell time, may be used to prevent therapy adjustments in response to transient posture states. Using a dwell time, only those posture states that are assumed by a patient for a minimum length of time will result in therapy adjustment. In some cases, different dwell times may be used for different posture state transitions.

To help ensure that the dwell time is set to an appropriate length of time, patient therapy adjustment data may be recorded and analyzed. Therapy adjustments made by the patient during the dwell time may indicate that the dwell time is too long. Likewise, therapy adjustments made by the patient after expiration of the dwell time may indicate that the dwell time is too short. Based on analysis of the patient therapy adjustment data, the dwell time can be adjusted to a length of time that is appropriate for the patient and/or posture state.

In one example, the disclosure provides a method comprising delivering therapy to a patient, detecting a posture state transition of a patient, upon expiration of a dwell time for the posture state transition, adjusting the therapy based on the posture state transition, detecting a patient adjustment of the therapy, and adjusting the dwell time based on the patient adjustment.

In another example, the disclosure provides a medical device comprising a posture state module that detects a posture state transition of a patient, a therapy module that delivers therapy to a patient, and a processor that, upon expiration of a dwell time for the posture state transition, adjusts the therapy based on the posture state transition, detects a patient adjustment of the therapy, and adjusts the dwell time based on the patient adjustment.

In a further example, the disclosure provides a medical system comprising a medical device that detects a posture state transition of a patient, and delivers therapy to a patient upon expiration of a dwell time for the posture state transition, an external programmer that receives a patient adjustment of the therapy, and a processor that adjusts the dwell time based on the patient adjustment.

In another example, the disclosure provides a computer-readable medium comprising instructions to cause a processor to deliver therapy to a patient, detect a posture state transition of a patient, upon expiration of a dwell time for the posture state transition, adjusting the therapy based on the posture state transition, detect a patient adjustment of the therapy, and adjust the dwell time based on the patient adjustment.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1A:
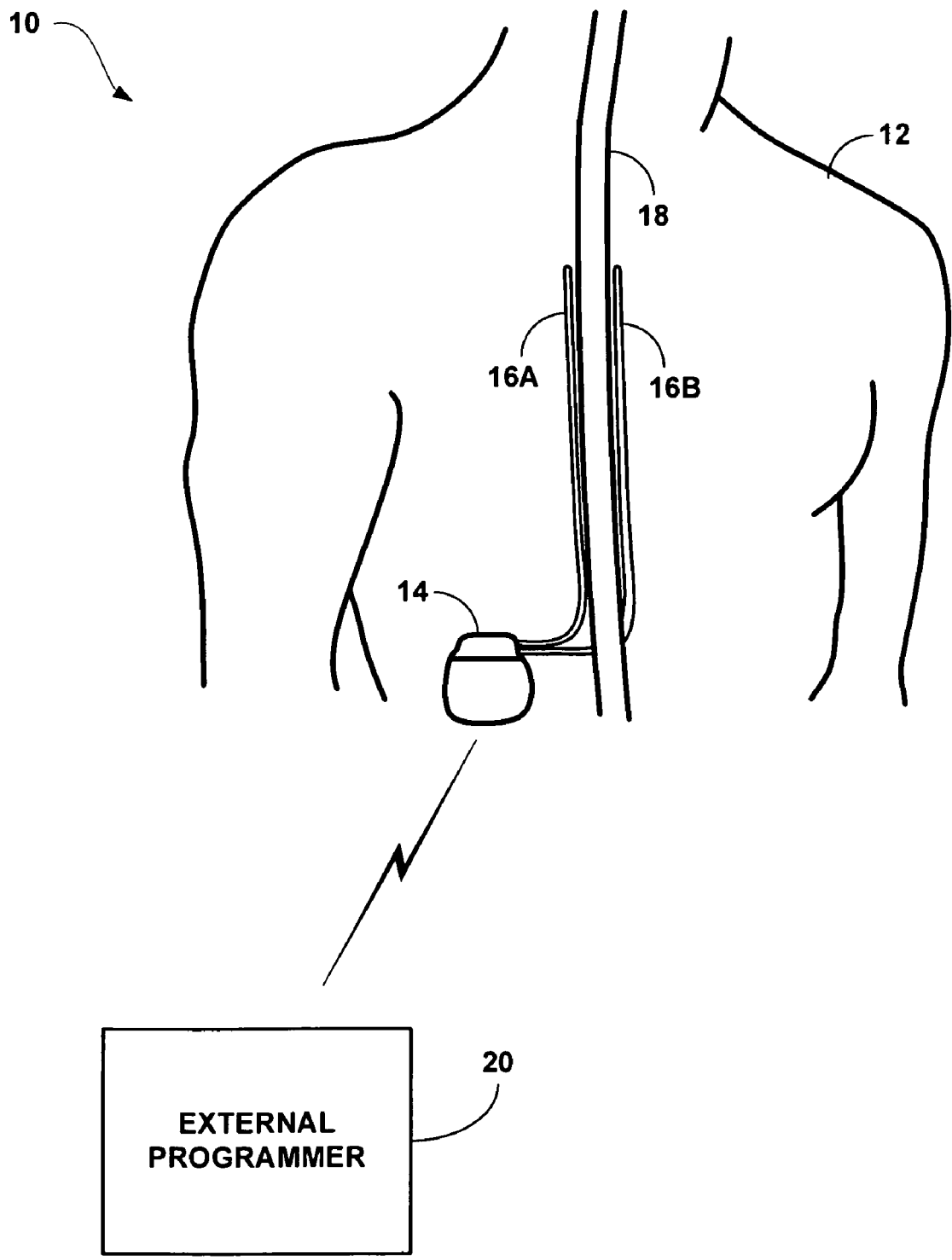
FIG. 1A is a conceptual diagram illustrating an implantable stimulation system including two implantable stimulation leads.

In some medical devices that deliver electrical stimulation therapy or other therapies, therapeutic efficacy may change as the patient changes posture states. In general, a posture state may refer to a posture or a combination of posture and activity. Efficacy may refer, in general, to a combination of a degree of alleviation of symptoms, alone or in combination with a degree of undesirable side effects.

Changes in posture state may cause changes in efficacy due to changes in distances between electrodes or other therapy delivery elements, e.g., due to temporary migration of leads or catheters caused by forces or stresses associated with different postures, or from changes in compression of patient tissue in different posture states. Also, posture state changes may present changes in symptoms or symptom levels, e.g., pain level. For example, for a given patient, sitting may be more painful than standing, or standing may be associated with physical activity that presents more pain.

Changes in efficacy for different posture states may require the patient to continually manage therapy for different posture states by manually adjusting therapy. To maintain therapeutic efficacy, it may be desirable to automatically adjust therapy based on detection of different patient posture states. A medical device may use a posture state module that detects patient posture state. The medical device may adjust therapy in response to different posture states detected by the posture state module.

Adjustment of therapy may refer to adjustment of therapy parameters or selection of different therapy programs or groups of programs defining different sets of therapy parameters. Therapy adjustments in response to different posture states may be fully automatic, semi-automatic in the sense that a user may provide approval of proposed changes, or user-directed in the sense that the patient may manually adjust therapy based on a posture state detection.

A patient posture state may be transient, i.e., brief or temporary. To avoid adjusting therapy in response to transient posture states, a time delay may be imposed. The time delay, which may be referred to as a dwell time, may be used to prevent therapy adjustments in response to transient posture states. Using a dwell time, only those posture states that are assumed by a patient for a minimum length of time will result in therapy adjustment. In particular, the dwell time may ensure that a posture state is stable before therapy is adjusted based on the posture state. In some cases, different dwell times may be used for different posture state transitions.

After a patient is classified in a posture state, a medical device may be configured to delay therapy adjustment until expiration of the dwell time, indicating a stable posture state. If the posture state changes before the dwell time expires, the medical device does not make a therapy adjustment associated with the detected posture state. If the selected posture state remains unchanged for the duration of the dwell time, indicating a stable posture state, the medical device activates the therapy adjustment associated with the posture state.

Hence, a dwell time may be used to prevent posture states that are only temporarily assumed from affecting therapy or initiating some other action, such as issuance of a notification, establishment of a communication session, or storing of data. Instead, only those posture states that are assumed by a patient for some required length of time will result in the initiation of some action.

To help ensure that the dwell time is set to an appropriate length of time, patient therapy adjustment data may be recorded and analyzed. Therapy adjustments made by the patient during the dwell time may indicate that the dwell time is too long. Likewise, therapy adjustments made by the patient after expiration of the dwell time may indicate that the dwell time is too short. Based on analysis of the patient therapy adjustment data, the dwell time can be adjusted to a length of time that is appropriate for the patient and/or posture state.

When manual therapy adjustments occur during the dwell time, a medical device or another device such as a programmer may determine whether the manual therapy adjustments are consistent with therapy adjustments that may automatically occur in response to the posture state transition. When manual therapy adjustment occur following expiration of the dwell time, the medical device or other device may also determine whether the therapy adjustments are consistent with returning close to or toward a therapy delivered prior to the automatic therapy adjustment at the end of the dwell time. The manner in which user-initiated therapy adjustments modify therapy delivery may be used to confirm that a dwell time adjustment is appropriate.

To help ensure that the dwell time is set to an appropriate length of time, the medical device and/or programmer that communicates with the medical device may record and analyze therapy adjustment data. Therapy adjustments are user-initiated, e.g., patient-initiated, and may be specified manually or by other media such as voice recognition or the like. In each case, therapy adjustment may be entered via a programmer that communicates with the medical device, which may be an IMD.

When a patient adjusts therapy following the detection of a posture state but before expiration of the dwell time, the patient may be seeking to more quickly transition to a particular therapy setting upon reaching the posture state. For example, that patient may not want to wait for automated therapy adjustment to be applied upon expiration of the dwell time. Instead, the patient may desire rapid adjustment to ensure adequate coverage of symptoms when the patient assumes the posture state. In this case, the dwell time may be too long and should be shortened. By shortening the length of the dwell time, the medical device may respond more quickly to the detected posture state, providing the therapy adjustment sooner, e.g., so that the patient receives appropriate therapy for more effective coverage of symptoms for the detected posture state.

Alternatively, if the patient adjusts therapy following detection of a posture state and after expiration of the dwell time, and the adjustment tends to return close to or toward the therapy delivered for the previous posture state, it may be determined that the patient is not yet in need of the therapy adjustment for the newly detected posture state. In particular, in some cases, a patient may not begin to feel any adverse effect on efficacy until some period of time after a posture state has stabilized, i.e., until some time after the dwell time. Until that time, the patient may feel more comfortable with the previous therapy parameters delivered for the previous posture state. When the patient begins to feel adverse effects, such as a decrease in pain coverage, the patient may desire to make a therapy adjustment associated with the newly detected posture state. By increasing the length of the dwell time based on analysis of therapy adjustment data, the medical device may apply the therapy adjustment not only after the posture state has stabilized but also at a time that the therapy adjustment will be more appropriate, given the patient's delayed response to the posture state change.

FIG. 1A is a schematic diagram illustrating an implantable stimulation system 10 including a pair of implantable electrode arrays in the form of stimulation leads 16A and 16B. Although the techniques described in this disclosure may be generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable spinal cord stimulation (SCS) system for purposes of illustration, but without limitation as to other types of medical devices.

As shown in FIG. 1A, system 10 includes an IMD 14 and external programmer 20 shown in conjunction with a patient 12. In the example of FIG 1A, IMD 14 is an implantable electrical stimulator configured for SCS, e.g., for relief of chronic pain or other symptoms. Again, although FIG. 1A shows an implantable medical device, other examples may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as SCS to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, or gastroparesis. In this manner, system 10 may be configured to provide therapy taking the form of deep brain stimulation (DBS), pelvic floor stimulation, gastric stimulation, or any other stimulation therapy. In addition, patient 12 is ordinarily a human patient.

Each of leads 16 may include electrodes (not shown in FIG. 1), and the parameters for a program that controls delivery of stimulation therapy by IMD 12 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 12 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some cases, an external stimulator may be a trial or screening stimulation that is used on a temporary basis to evaluate potential efficacy to aid in consideration of chronic implantation for a patient. In additional examples, IMD 14 may be a leadless stimulator with one or more arrays of electrodes arranged on a housing of the stimulator rather than leads that extend from the housing.

The stimulation may be delivered via selected combinations of electrodes carried by one or both of leads 16. The target tissue may be any tissue affected by electrical stimulation energy, such as electrical stimulation pulses or waveforms. Such tissue includes nerves, smooth muscle, and skeletal muscle. In the example illustrated by FIG. 1A, the target tissue is spinal cord 18. Stimulation of spinal cord 18 may, for example, prevent pain signals from traveling through the spinal cord and to the brain of patient 12. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry one or more arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different pain therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 delivers stimulation therapy according to one or more programs. A program defines one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, leads 16 may migrate toward IMD 14 when patient 12 bends over, resulting in displacement of electrodes and possible disruption in delivery of effective therapy. For example, stimulation energy transferred to target tissue may be reduced due to electrode migration, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this case, the amplitude of stimulation therapy may need to be decreased to avoid causing patient 12 additional pain or unusual sensations, which may be considered undesirable side effects that undermine overall efficacy.

Many other examples of reduced efficacy due to increased coupling or decreased coupling of stimulation energy to target tissue may occur due to changes in posture and/or activity level associated with patient posture state. To avoid or reduce possible disruptions in effective therapy due to posture state changes, IMD 14 may include or be associated with a posture state module that detects the posture state of patient 12 and causes the IMD 14 to automatically adjust stimulation according to the detected posture state. For example, a posture state module may include a posture state sensor such as an accelerometer that detects when patient 12 lies down, stands up, or otherwise changes posture.

In response to a posture state indication by the posture state module, IMD 14 may make a therapy adjustment. For example, IMD 14 may change program group, program, stimulation amplitude, pulse width, pulse rate, and/or one or more other parameters, groups or programs to maintain therapeutic efficacy. When patient 12 lies down, for example, IMD 14 may automatically reduce stimulation amplitude so that patient 12 does not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change. Additionally, in response to a posture state change, IMD 14 may communicate with external programmer 20 to provide a notification to a user, such a clinician, that patient 12 has potentially experienced a fall.

A user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

A user interface of external programmer 20 may indicate to the user the posture state in which patient 12 currently resides. This patient posture state may be a static posture that does not take into account activity level, an activity level that does not take into account posture, or some combination of the posture and activity level that describes the physical position and movement of patient 12. As an example, posture may be characterized as one of the following postures: standing, sitting, lying down on back, lying down on front, lying down on left side, lying down on right side. Activity level may be characterized as one of high, medium and low, or be characterized in terms of a numeric scale, e.g., 1-10 or 1-12. In other examples, other gradations, e.g., high, medium high, medium, medium low, and low, or other numerical scales may be used to characterize activity level.

A posture state may indicate a combination of one of the above postures with one of the above activity levels. For some postures, such as lying down postures, the posture state may not need to consider activity level, as the patient may be less likely to undertake any significant activity in such postures. In other cases, all posture states may take into account posture and activity level, even if there is minimal activity in a particular posture. Posture state may be determined based on posture information and/or activity level information generated by a posture state module, which may include one or more accelerometers or other posture or activity level sensors.

A patient posture state may be represented by a posture state indication presented by the user interface of programmer 20 as a visible, audible, or tactile indication. When presented as a visible indication, the posture state indication may be, for example, a graphical representation, a symbolic icon, a textual representation, such as word or number, an arrow, or any other type of indication. The visible indication may be presented via a display, such as an a liquid crystal display (LCD), dot matrix display, organic light-emitting diode (OLED) display, touch screen, or the like. In other cases, the visible indication may be provided in a translucent area that is selectively backlit to indicate a posture. An audible indication may be produced by programmer 20 as spoken words stating a posture state, or different audible tones, different numbers of tones, or other audible information generated by the programmer to indicate posture state. A tactile indication of posture state may be produced by programmer 20, for example, in the form of different numbers of vibratory pulses delivered in sequence or vibratory pulses of different lengths, amplitudes, or frequencies.

Programmer 20 may present multiple indications representative of different patient posture states. IMD 14 may communicate a patient posture state according to a posture state parameter value sensed by a posture state module to external programmer 20, e.g., by wireless telemetry. For example, IMD 14 may transmit a posture state indication to programmer 20 on a periodic, intermittent or continuous basis or in response to a posture state change. Alternatively, programmer 20 may request a posture state indication from IMD 14 on a periodic, intermittent or continuous basis. External programmer 20 then may select and present the associated posture state indication.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany patient 12 throughout the patient's daily routine. In general, a physician or clinician programmer may support selection and generation of programs by a clinician for use by stimulator 14, whereas a patient programmer may support adjustment and selection of such programs by a patient during ordinary use.

IMD 14 may be constructed with a biocompatible housing, such as titanium or stainless steel, or a polymeric material such as silicone or polyurethane, and surgically implanted at a site in patient 18 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

At the distal tips of leads 16 are one or more electrodes (not shown) that transfer the electrical stimulation from the lead to the tissue. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Figure 1B:
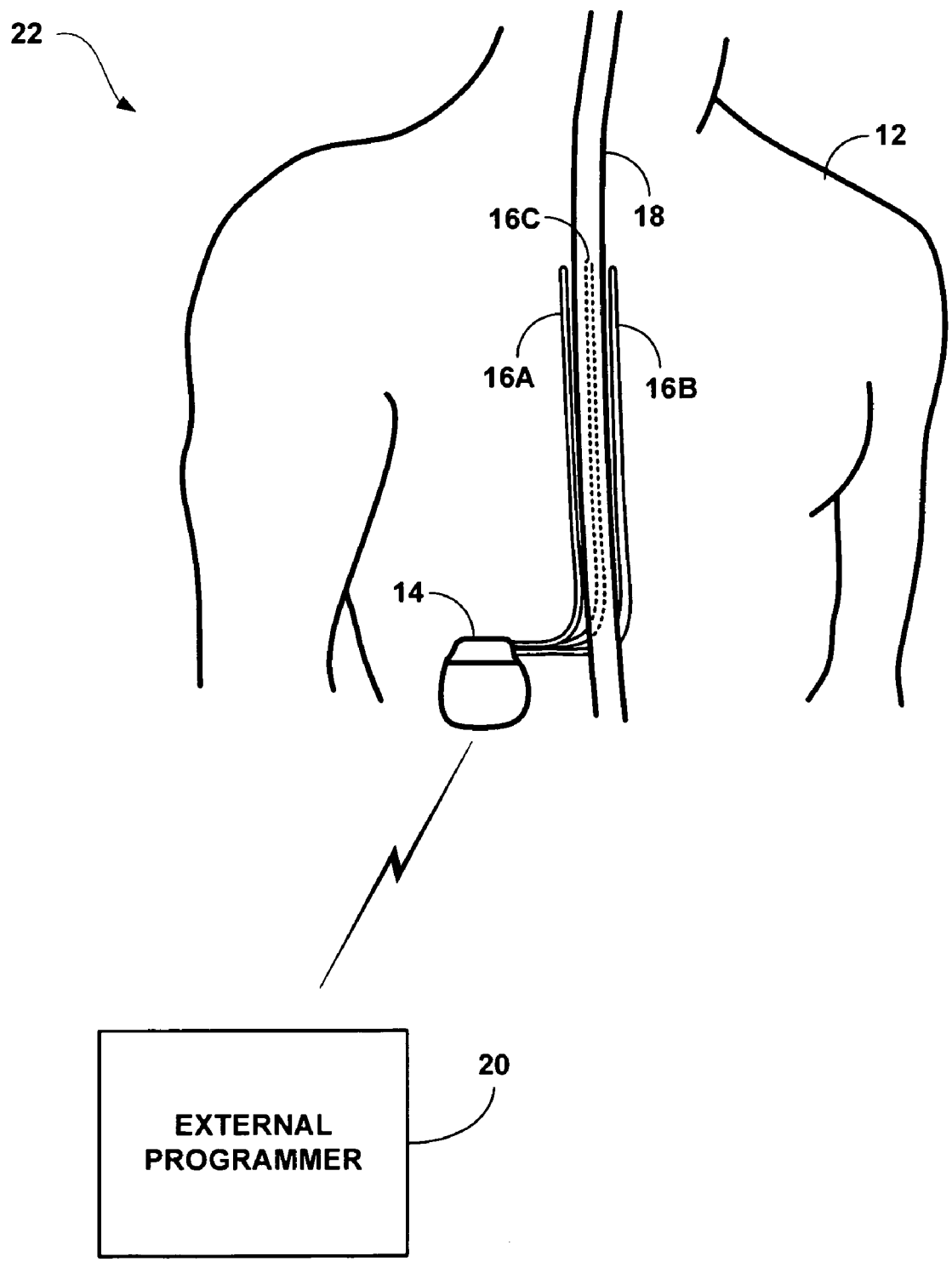
FIG. 1B is a conceptual diagram illustrating an implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. External programmer 20 may be initially told the number and configuration of leads 16 in order to appropriately program stimulation therapy.

For example, leads 16A and 16B could include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
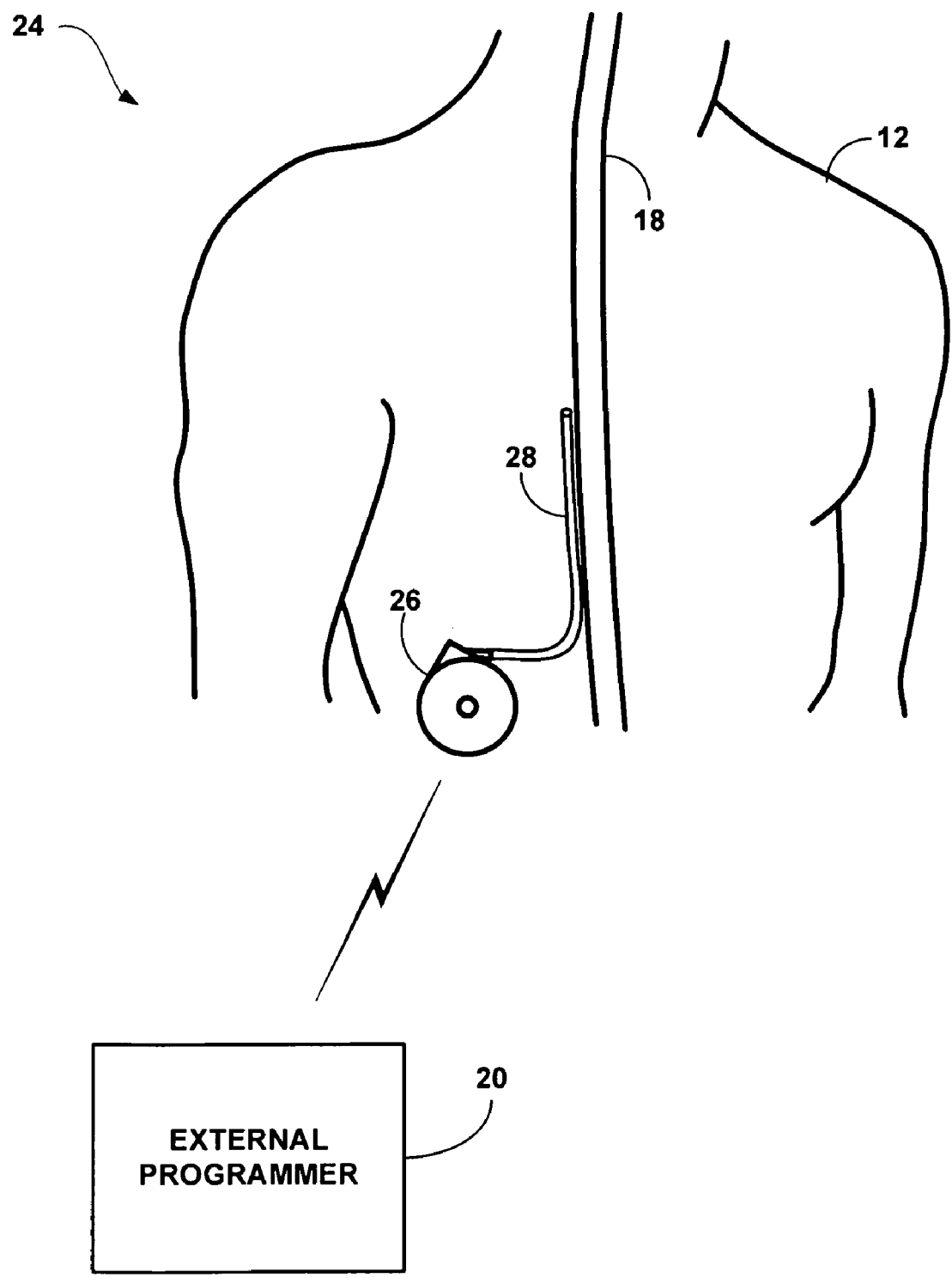
FIG. 1C is a conceptual diagram illustrating an implantable drug delivery system including a delivery catheter.

FIG. 11C is a conceptual diagram illustrating an implantable drug delivery system 24 including one delivery catheter 28 coupled to IMD 26. As shown in the example of FIG 1C, drug delivery system 24 is substantially similar to systems 10 and 22. However, drug delivery system 24 performs the similar therapy functions via delivery of drug stimulation therapy instead of electrical stimulation therapy. IMD 26 functions as a drug pump in the example of FIG 1C, and IMD 26 communicates with external programmer 20 to initialize therapy or modify therapy during operation. In addition, IMD 26 may be refillable to allow chronic drug delivery.

Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 26 may be an external device which includes a percutaneous catheter that forms catheter 28 or that is coupled to catheter 28, e.g., via a fluid coupler. In other examples, IMD 26 may include both electrical stimulation as described in IMD 14 and drug delivery therapy.

IMD 26 may also operate using parameters that define the method of drug delivery. IMD 26 may include programs, or groups of programs, that define different delivery methods for patient 14. For example, a program that controls delivery of a drug or other therapeutic agent may include a titration rate or information controlling the timing of bolus deliveries. Patient 14 may use external programmer 20 to adjust the programs or groups of programs to regulate the therapy delivery.

Similar to IMD 14, IMD 26 may include a posture state module that monitors the posture state of patient 12 and adjusts therapy accordingly. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Figure 2:
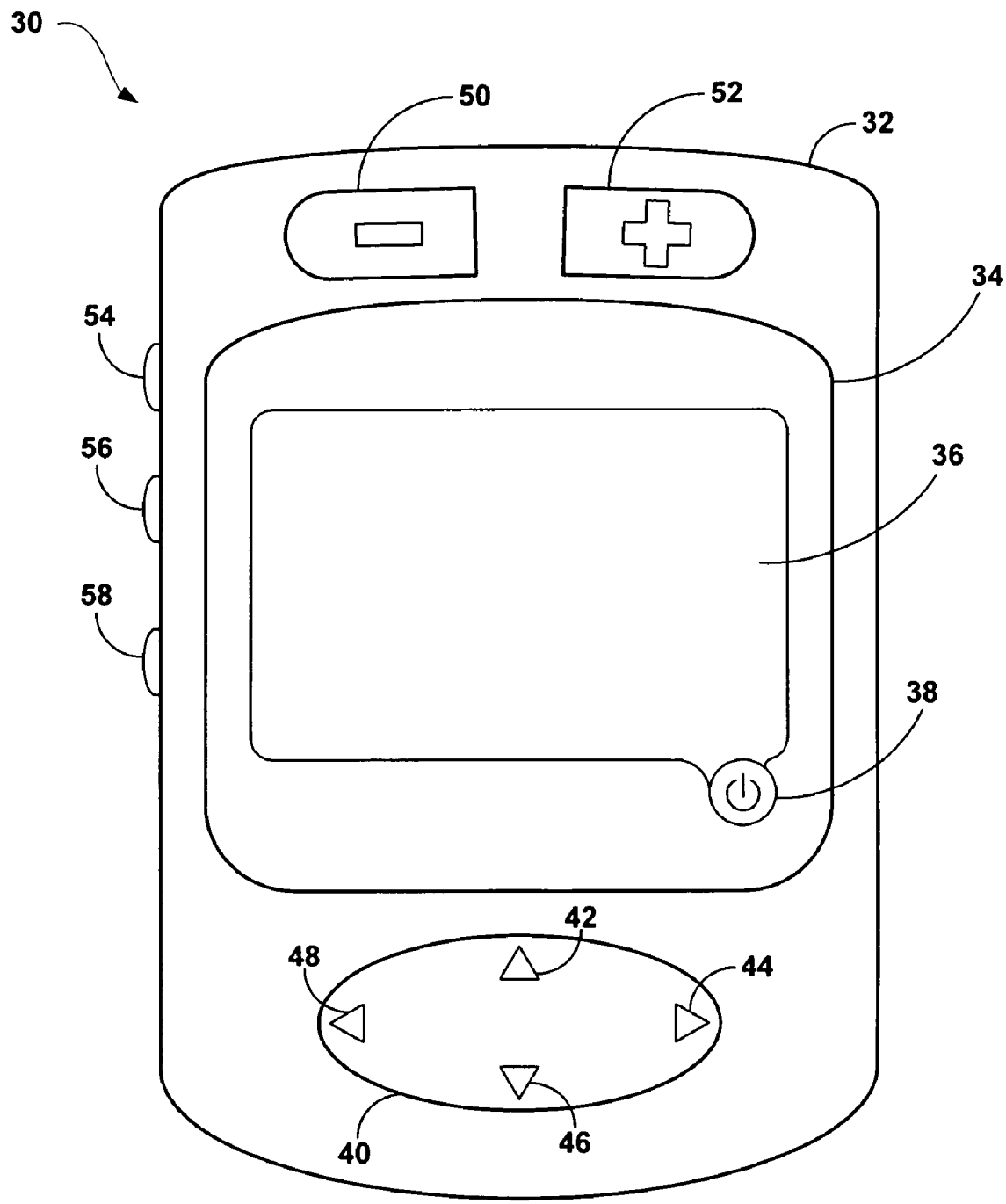
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an implantable medical device. A patient may use programmer 30 to enter therapy adjustments. For example, using programmer 30 a patient may select programs, select program groups, and/or adjust program parameters such as amplitude, pulse width, pulse rate, electrode combination or electrode polarity. Patient programmer 30 is an example of external programmer 20 illustrated in FIGS. 1A, 1B and 1C and may be used with either IMD 14 or IMD 26. In alternative examples, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which encloses circuitry necessary for patient programmer 30 to operate.

Patient programmer 30 also includes display 36, power button 38, increase button 52, decrease button 50, sync button 58, stimulation ON button 54, and stimulation OFF button 56. Cover 34 protects display 36 from being damaged during patient programmer 30 use. Patient programmer 30 also includes control pad 40 which allows a user to navigate through items displayed on display 36 in the direction of arrows 42, 44, 46, and 48. In some examples, the buttons and pad 40 may take the form of soft keys (e.g., with functions and contexts indicated on display 36), with functionality that may change, for example, based on current programming operation or user preference. In alternative examples, display 36 may be a touch screen in which patient 12 may interact directly with display 36 without the use of control pad 40 or even increase button 52 and decrease button 50.

Using various buttons, touchscreen media, or other input media, patient 12 may be enter manual therapy adjustments. If posture-response therapy is enabled to automatically adjust therapy based on detected posture state, patient 12 may also have the ability to manually adjust therapy, either completely or to a limited degree. For example, when IMD 14 or 26 adjusts stimulation therapy based on detected posture state, patient 12 also may adjust the therapy, e.g., by adjusting voltage or current amplitude, pulse width or pulse rate, or by selecting different programs or program groups. Patient therapy adjustments may be entered before, after or during the running of dwell time following a posture state detection.

In the illustrated example, patient programmer 30 is a hand held device. Patient programmer 30 may accompany patient 12 throughout a daily routine. In some cases, patient programmer 30 may be used by a clinician when patient 12 visits the clinician in a hospital or clinic. In other examples, patient programmer 30 may be a clinician programmer that remains with the clinician or in the clinic and is used by the clinician and/or patient 12 when patient 12 is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52.

In some examples, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may be a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMD 14 or 26. For example, patient programmer 30 may provide a scrollable list of groups, and a scrollable list of programs within each group, via display 36.

Control pad 40 allows patient 12 to navigate through items displayed on display 36. Patient 12 may press control pad 40 on any of arrows 42, 44, 46, and 48 in order to move to another item on display 36 or move to another screen not currently shown on the display. In some examples, pressing the middle of control pad 40 may select any item highlighted in display 36. In other examples, scroll bars, a scroll wheel, individual buttons, or a joystick may perform the complete or partial functions of control pad 40. In alternative examples, control pad 40 may be a touch pad that allows patient 12 to move a cursor within the user interface displayed on display 36 to manage therapy.

Decrease button 50 and increase button 52 provide an input mechanism for patient 12. In general, decrease button 50 may decrease the value of a highlighted stimulation parameter, e.g., amplitude, pulse width or pulse rate, every time the decrease button is pressed. In contrast, increase button 52 may increase the value of a highlighted stimulation parameter one step every time the increase button is pressed. While buttons 50 and 52 may be used to control the value of any stimulation parameter, buttons 50 and 52 may also control patient feedback input. When either of buttons 50 and 52 is selected, patient programmer 30 may initialize communication with IMD 14 or 26 to change therapy accordingly.

When depressed by patient 12, stimulation ON button 54 directs programmer 30 to generate a command for communication to IMD 14 that turns on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some examples, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display 36 brightness and contrast, or other similar options. In alternative examples, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described in this disclosure. Alternative examples of patient programmer 30 may include other input mechanisms such as a keypad, microphone, camera lens, or any other media input that allows the user to interact with the user interface provided by patient programmer 30.

In alternative examples, the buttons of patient programmer 30 may perform different functions than the functions provided in FIG. 2 as an example. In addition, other examples of patient programmer 30 may include different button layouts or different numbers of buttons. For example, patient programmer 30 may even include a single touch screen that incorporates all user interface functionality with a limited set of buttons or no other buttons.

Figure 3:
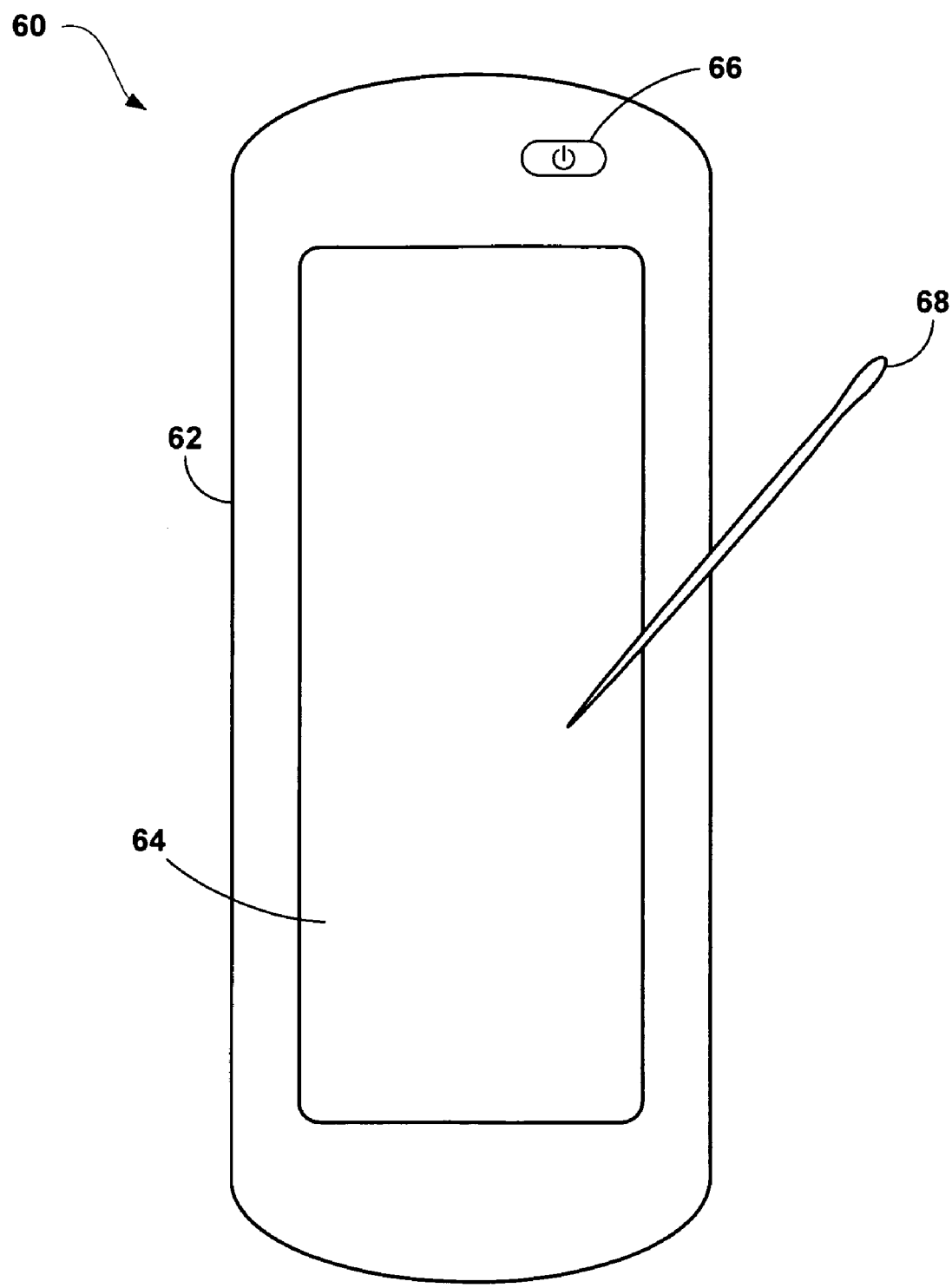
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an implantable medical device. Clinician programmer 60 is an example of external programmer 20 illustrated in FIGS. 1A, 1B and 1C and may be used with either IMD 14 or IMD 26. In alternative examples, clinician programmer 60 may be used with an external medical device. Using programmer 60, a user may make any of a variety of therapy adjustments. As shown in FIG. 3, clinician programmer 60 provides a user interface (not shown) for a user, such as a clinician, physician, technician, or nurse, to manage and program stimulation therapy. Clinician programmer 60 is protected by housing 62, which encloses circuitry necessary for clinician programmer 60 to operate.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some examples, the user may be able to touch display 64 with a finger, pen, or any other pointing device. In alternative examples, clinician programmer 60 may include one or more buttons, keypads, control pads, touch pads, or other devices that accept user input, similar to patient programmer 30.

In the illustrated example, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some examples, clinician programmer 60 may be a larger device that may be less portable, such as a notebook computer, workstation, or even a remote computer that communicates with IMD 14 or 26 via a remote telemetry device.

In some implementations, most, if not all, of clinician programmer 60 functions may be completed via the touch screen of display 64. The user may program stimulation therapy, modify programs or groups, retrieve stored therapy data, retrieve posture state information, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
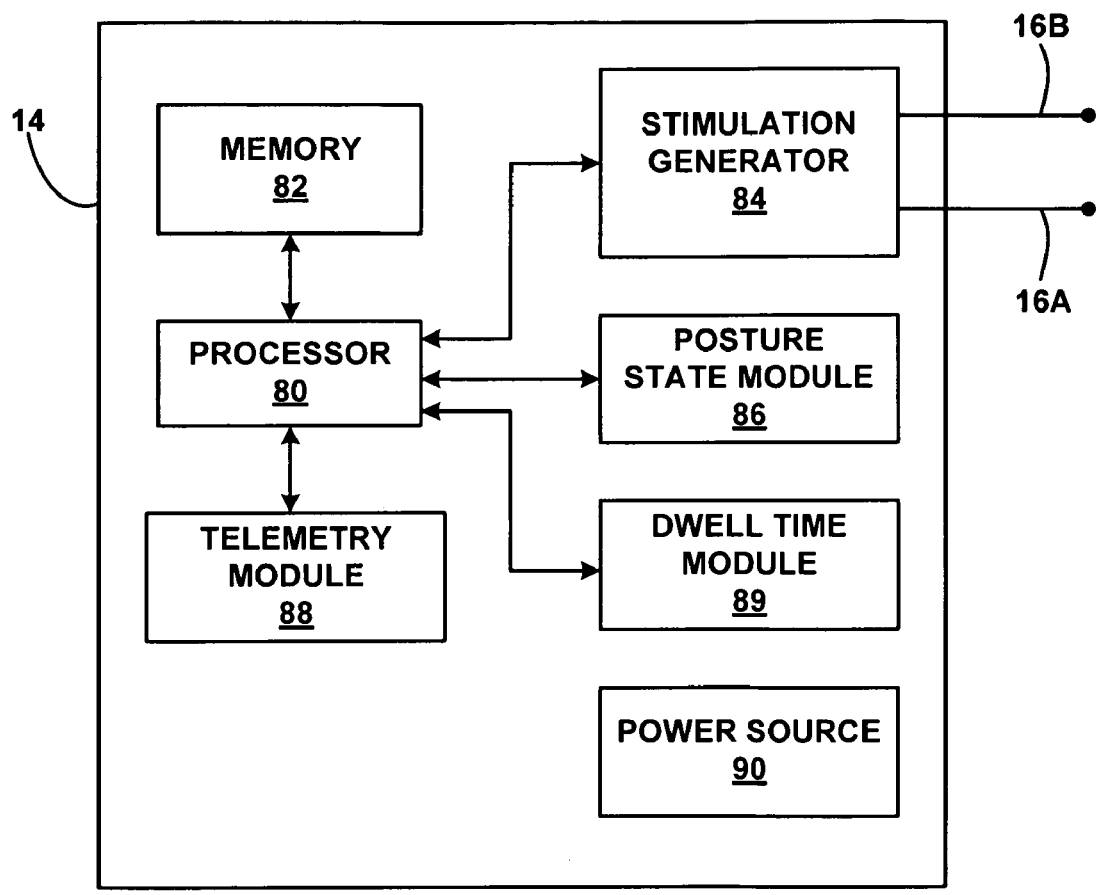
FIG. 4 is a functional block diagram illustrating various components of an implantable electrical stimulator.

FIG. 4 is a functional block diagram illustrating various components of an IMD 14. In the example of FIG. 4, IMD 14 includes a processor 80, memory 82, stimulation generator 84, posture state module 86, telemetry module 88, dwell time module 89, and power source 90. Memory 82 may store instructions for execution by processor 80, stimulation therapy data, posture state information, posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

In some examples, IMD 14 may send raw posture state data or posture state detections to an external programmer, such as programmer 30 or 60, and the programmer may apply a dwell time and then send instructions to IMD 14 to adjust therapy. In the example of FIG. 4, however, posture state detection and dwell time analysis are performed within IMD 14, which adjusts therapy according to therapy associated with a particular posture state after that posture state is detected and the dwell time has expired. Again, therapy adjustment may include adjustment of one or more therapy parameters such as amplitude, pulse width, pulse rate, or electrode combination or polarity, or selection of different programs or program groups. IMD 14 may be configured to analyze manual therapy adjustments with respect to the dwell time, and automatically adjust dwell time length based on the analysis. Alternatively, IMD 14 may send manual therapy adjustment and timing information to an external programmer 30 or 60 for analysis and adjustment of the dwell time used by IMD 14.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other examples, stimulation generator 84 may include multiple current or voltage sources to drive more than one electrode combination at one time. In this case, stimulation generator 84 may decrease a stimulation amplitude (e.g., a current or voltage amplitude) to the first electrode combination and simultaneously increase a stimulation amplitude to the second electrode combination to shift the stimulation therapy.

An electrode combination may be represented by a data stored in a memory location, e.g., in memory 82, of IMD 14. Processor 80 may access the memory location to determine the electrode combination and control stimulation generator 84 to deliver electrical stimulation via the indicated electrode combination. To change electrode combinations, amplitudes, pulse rates, or pulse widths, processor 80 may direct stimulation generator 84 to make the appropriate changes to therapy according to instructions within memory 82 and rewrite the memory location to indicate the changed therapy. In other examples, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12. Processor 80 also may control telemetry module 88 to send and receive information to and from external programmer 20. For example, telemetry module 88 may send information to and receive information from patient programmer 30. An example range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and 1200 Hz, more preferably between approximately 5 Hz and 250 Hz, and still more preferably between approximately 30 Hz and 130 Hz.

2. Amplitude: between approximately 0.1 volts and 50 volts, more preferably between approximately 0.5 volts and 20 volts, and still more preferably between approximately 1 volt and 10 volts. In other examples, a current amplitude may be defined as the biological load in the voltage that is delivered. For example, the range of current amplitude may be between 0.1 milliamps (mA) and 50 mA.

3. Pulse Width: between about 10 microseconds and 5000 microseconds, more preferably between approximately 100 microseconds and 1000 microseconds, and still more preferably between approximately 180 microseconds and 450 microseconds.

In other applications, different ranges of parameter values may be used. For deep brain stimulation (DBS), as one example, alleviation or reduction of symptoms associated with Parkinson's disease, essential tremor, epilepsy or other disorders may make use of stimulation having a pulse rate in the range of approximately 0.5 to 1200 Hz, more preferably 5 to 250 Hz, and still more preferably 30 to 185 Hz, and a pulse width in the range of approximately 10 microseconds and 5000 microseconds, more preferably between approximately 60 microseconds and 1000 microseconds, still more preferably between approximately 60 microseconds and 450 microseconds, and even more preferably between approximately 60 microseconds and 150 microseconds. Amplitude ranges such as those described above with reference to SCS, or other amplitude ranges, may be used for different DBS applications.

Processor 80 stores stimulation parameters in memory 82, e.g., as programs and groups of programs. Upon selection of a particular program group, processor 80 may control stimulation generator 84 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads.

Posture state module 86 allows IMD 14 to sense the posture state of patient 12, e.g., posture, activity or any other static position or motion of patient 12. In the example of FIG. 4, posture state module 86 may include one or more accelerometers, such as three-axis accelerometers, capable of detecting static orientation or vectors in three-dimensions. For example, posture state module 86 may include one or more micro-electro-mechanical accelerometers. In other examples, posture state module 86 may alternatively or additionally include one or more gyroscopes, pressure transducers or other sensors to sense the posture state of patient 12. Posture state information generated by posture state module 86 and processor 80 may correspond to an activity and/or posture undertaken by patient 12 or a gross level of physical activity, e.g., activity counts based on footfalls or the like.

In some examples, processor 80 processes the analog output of the posture state sensor in posture state module 86 to determine activity and/or posture data. For example, processor 80 or a processor of posture state module 86 may process the raw signals provided by the posture state sensor to determine activity counts. In some examples, processor 80 may process the signals provided by the posture state sensor to determine velocity of motion information along each axis.

In one example, each of the x, y, and z signals provided by the posture state sensor has both a DC component and an AC component. The DC components may describe the gravitational force exerted upon the sensor and may thereby be used to determine orientation of the sensor within the gravitational field of the earth. Assuming the orientation of the sensor is relatively fixed with respect to patient 12, the DC components of the x, y and z signals may be utilized to determine the patient's orientation within the gravitational field, and hence to determine the posture of patient 12.

The AC component of the x, y and z signals may yield information about patient motion. In particular, the AC component of a signal may be used to derive a value for an activity describing the patient's motion. This activity may involve a level, direction of motion, or acceleration of patient 12.

One method for determining the activity is an activity count. An activity count may be used to indicate the activity or activity level of patient 12. For example, a signal processor may sum the magnitudes of the AC portion of an accelerometer signal for "N" consecutive samples. For instance, assuming sampling occurs as 25 Hz, "N" may be set to 25, so that count logic provides the sum of the samples that are obtained in one second. This sum may be referred to as an "activity count."

The number "N" of consecutive samples may be selected by processor 80 or a processor of posture state module 86 based on the current posture state, if desired. The activity count may be the activity portion of the posture state parameter value that may be added to the posture portion. The resulting posture state parameter value may then incorporate both activity and posture to generate an accurate indication of the motion of patient 12.

As another example, the activity portion of the posture state parameter value may describe a direction of motion. This activity parameter may be associated with a vector and an associated tolerance, which may be a distance from the vector. Another example of an activity parameter relates to acceleration. A value quantifying a level of change of motion over time in a particular direction may be associated with the activity portion of a posture state parameter value.

Posture state information from posture state module 86 may be stored in memory 82 for later review by a clinician, used to adjust therapy, present a posture state indication to patient 12, or some combination thereof. As an example, processor 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture.

IMD 14 may also store which group or program was being used to deliver therapy when patient 12 was in the sensed posture. Further, processor 80 may also adjust therapy for a new posture when posture state module 86 indicates that patient 12 has in fact changed postures. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

A posture state parameter value from posture state module 86 that indicates the posture state may constantly vary throughout the day of patient 12. However, a certain activity (e.g., walking, running, or biking) or a posture (e.g., standing, sitting, or lying down) may include multiple posture state parameter values from posture state module 86. Memory 82 may include definitions for each posture state of patient 12. In one example, the definitions of each posture state may be illustrated as a cone in three-dimensional space. Whenever the posture state parameter value, e.g., a vector, from the three-axis accelerometer of posture state module 86 resides within a predefined posture volume, such as a cone, or is close to a reference posture vector, processor 80 indicates that patient 12 is in the posture state corresponding to the posture volume or the reference posture vector. A cone is described for purposes of example. Other definitions of posture states may be illustrated as other shapes, e.g., donuts or toroids, in three-dimensional space. In other examples, posture state parameter value from the 3-axis accelerometer may be compared to a look-up table value or equation to determine the posture state in which patient 12 currently resides.

Posture responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 12 to, for example, depress one or more keys of patient programmer 30 multiple times during the patient posture state to maintain adequate symptom control. In some examples, patient 12 may eventually be able to enjoy posture state responsive stimulation therapy without the need to continue making changes for different postures via patient programmer 30. Instead, patient 12 may transition immediately or over time to fully automatic adjustments based on posture state.

Although posture state module 86 is described as containing a 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the posture state of patient 12 may be determined from multiple posture state sensors placed at various locations on or within the body of patient 12.

In other examples, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some examples, to confirm or reject changes in sensed posture state that may result from vibration, patient travel (e.g., in an aircraft, car or train), or some other false positive of posture state.

Dwell time module 89 may be used to ensure that once posture state module 86 classifies patient 12 in a posture state, patient 12 does not exit that posture state for a predetermined dwell time, e.g., a delay time imposed between the time posture state module 86 detects a new posture state of patient 12 and the time processor 80 controls stimulation generator 84 to initiate a therapy adjustment in response to this detected posture state. If patient 12 does exit the posture state before the dwell time elapses, no actions are taken in response to classification of patient 12 in this posture state. In one example, only after this dwell time has elapsed will any actions such as therapy adjustments or notifications be taken in response to the classification. In this manner, dwell times are utilized to ensure that transitory posture states that patient 12 may occupy for only a short period of time will not prompt actions such as an unwanted change in therapy.

Moreover, the use of dwell times prevents a patient who is occupying a posture state that is at a boundary between two posture state definitions from triggering multiple actions (e.g., multiple therapy modifications) as patient 12 transitions between the two posture states over a short period of time. By selection of appropriate dwell times, an action in response to such short-term and repeated posture state re-classifications will be suppressed. An action (e.g., therapy change) will only be initiated after patient 12 finally settles in a stable manner into one or the other of the two posture states. This use of a dwell time introduces stability into the system, such that temporarily assumed, transient posture states do not result in the initiation of therapy changes or other posture state-responsive actions.

In one example, dwell time module 89 accesses current posture state information from posture state module 86.

Dwell time module 89 may also store an indication of the posture state that patient 12 was most-recently classified in a stable manner, e.g., the posture state that most-recently fulfilled the dwell time requirement. Dwell time module 89 compares this most recent stable posture state to the posture state detected by posture state module 86. If a mismatch occurs, indicating a change in posture state, a potential re-classification of the patient's posture state may be underway. According to one example of the current disclosure, before a response is initiated because of the posture state re-classification, a corresponding dwell time T is measured, as by a timer provided by dwell time module 89.

The posture state detected by posture state module 86 must remain stable throughout this dwell time T such that no other posture state re-classification by posture state module 86 occurs. If this stability is maintained, dwell time module 89 provides an indication to processor 80 that posture state reclassification occurred, and the processor proceeds to initiate the appropriate one or more responses for the detected posture state, such as adjustment of therapy voltage or current amplitude to an amplitude appropriate for the posture state. The appropriate responses may involve modification, cessation, or initiation of therapy delivery, storing of data, notification generation, an initiation or change in a communication session, and/or other responses involving system 10 or 22 (FIGS. 1A and 1B, respectively). On the other hand, if the dwell time does not expire before the posture state detected by posture state module 86 again changes, the dwell time is reset when posture state module 86 detects the change in posture state. The process may then be repeated if the newly detected posture state is different from the most-recently classified stable posture state.

The dwell time that is used by dwell time module 89 may be programmable. This value may be programmed by a clinician, for instance, when IMD 14 is being initialized, and may be re-programmed any time thereafter as desired by the clinician. In addition, different dwell times may be used for different posture state transitions. In one example, a dwell time may be automatically selected by processor 80 based on current system conditions. For example, the dwell time may be based, in full or in part, on the most-recently classified stable posture state. As another example, a newly-detected posture state may be used to select the dwell time. As a further example, the dwell time may be selected based on the transition from the patient's most-recent stable posture state to the newly-detected posture state.

Hence, different dwell times may be selected based on stable posture state, newly detected posture state, or a combination of the stable posture state and the detected posture state, e.g., based on the particular posture state transition running from the stable posture state to the detected posture state. If there are N different posture state transitions possible among M different posture states, then there may be N different dwell times used by dwell time module 89. In some examples, some posture state transitions may have the same dwell times while other posture state transitions may have different dwell times. As an illustration, if the set of possible posture states includes upright and active, upright and inactive, lying front, lying back, lying right, and lying left, then dwell time module 89 may apply different dwell times for transitions from upright and active to upright and inactive, upright and inactive to upright and active, upright and active to lying front, upright and inactive to lying back, upright and active to lying back, upright and inactive to lying back, lying back to lying front, lying right to lying left, lying left to lying back, and so forth.

In each case, a different dwell time may be selected based on the stable posture state and the newly detected posture state. As one example, if the patient's most-recently classified stable posture state is an upright posture state and the newly detected posture state is lying back, dwell time module 89 uses the dwell time for that transition. If the lying back posture state remains stable for the prescribed dwell time, then processor 80 may control stimulation generator 84 to adjust therapy from the therapy delivered for the upright posture state to the therapy delivered for the lying back posture state. The particular therapy adjustments may be programmed into memory 82, e.g., based on automated programming of therapy parameters and/or clinician-directed programming of therapy parameters for particular posture states. The dwell times may be stored in memory 82, e.g., in a lookup table, or other data structure.

In one example, the dwell time that is imposed by dwell time module 89 may be response-specific. In particular, different dwell times may be used for different actions taken by IMD 14. For example, once a re-classification of posture state occurs, a first dwell time may be imposed before processor 80 initiates a first response (e.g., an adjustment in therapy delivery). A second dwell time that is different from the first dwell time may be imposed before processor 80 initiates a second response (e.g., an event notification) and so on. If multiple dwell times are used, it is possible for the posture state classification to remain stable long enough to prompt a first action associated with a first dwell time. However, the posture state classification may change before a second, longer dwell time elapses. Therefore, the second action associated with this posture state classification is never initiated, since posture state stability was not achieved for the second, longer dwell time.

As may be appreciated, many examples are possible, including an approach that includes a single programmable dwell time for all posture states or posture state transitions, different programmable dwell times for different posture states or posture state transitions, or multiple dwell times for different posture state-responsive actions such as therapy adjustments and notifications. In other examples, dwell times may be automatically selected based on monitored system conditions. In a more flexible system, different dwell times may be selected for different types of responses. According to this latter technique, the multiple dwell times may be programmable, automatically selected based on system conditions or some combination thereof.

Wireless telemetry between IMD 14 and external programmer 20, e.g., patient programmer 30 or clinician programmer 60, or another device may be accomplished by radio frequency (RF) communication or proximal inductive interaction of IMD 14 with external programmer 20. Telemetry module 88 may send information to and receive information from external programmer 20 on a continuous basis, at periodic intervals, at non-periodic intervals, or upon request from the stimulator or programmer. To support RF communication, telemetry module 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. As one example, external programmer 20 may include the charger to recharge power source 90 of IMD 14. Hence, the programmer and charger may be integrated in the same device. Alternatively, in some cases, a charger unit may serve as an intermediate device that communicates with both the IMD and the programmer. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 5:
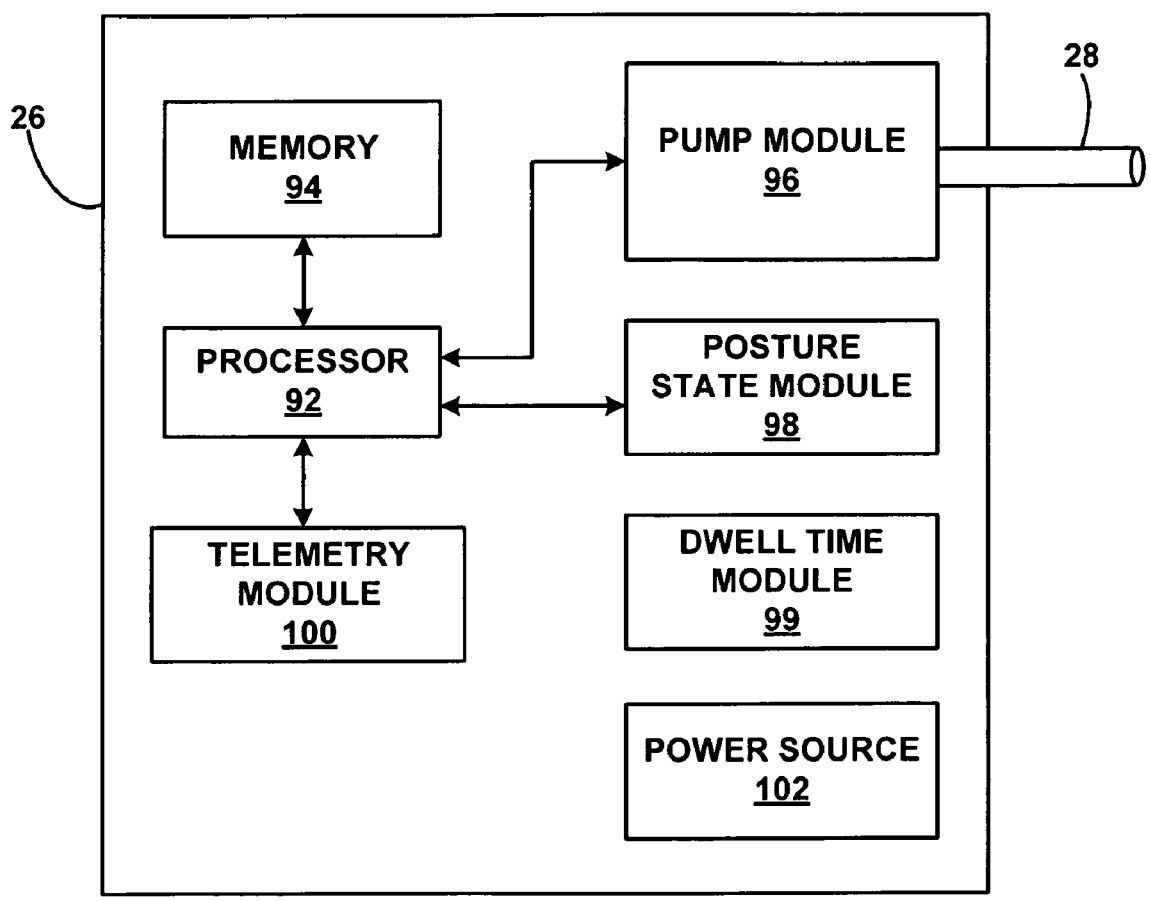
FIG. 5 is a functional block diagram illustrating various components of an implantable drug pump.

FIG. 5 is a functional block diagram illustrating various components of an IMD 26 that is a drug pump. IMD 26 is a drug pump that operates substantially similar to IMD 14 of FIG. 4. IMD 26 includes processor 92, memory 94, pump module 96, posture state module 98, dwell time module 99, telemetry module 100, and power source 102. Dwell time module 99 may be substantially similar to dwell time module 89 (FIG. 4) of IMD 14. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 may control pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state module 98 to adjust drug delivery therapy when patient 12 changes posture states, e.g., adjusts his (or her) posture.

Figure 6:
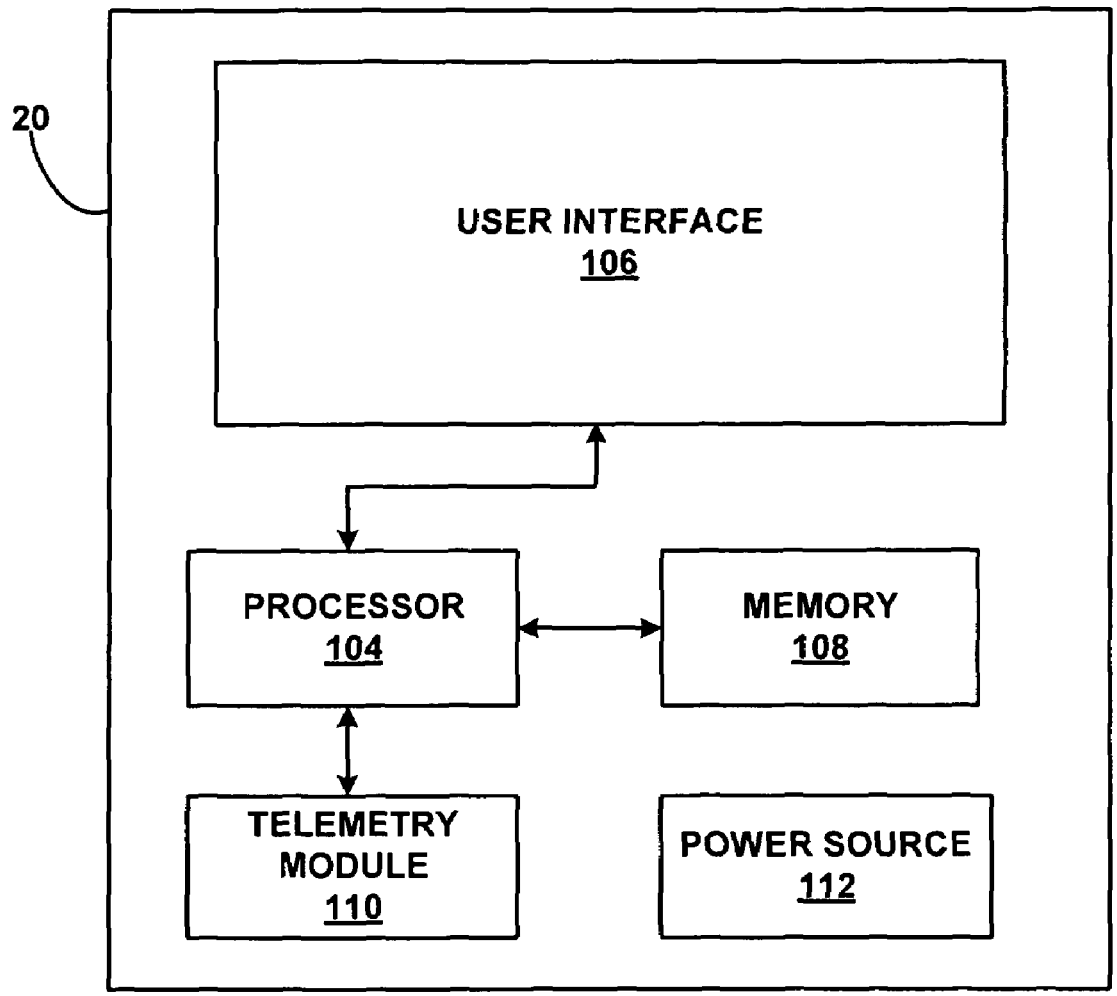
FIG. 6 is a functional block diagram illustrating various components of an external programmer for an implantable medical device.

FIG. 6 is a functional block diagram illustrating various components of an external programmer 20 for IMD 14 or 26. As shown in FIG. 6, external programmer 20 includes processor 104, memory 108, telemetry module 110, user interface 106, and power source 112. External programmer 20 may be embodied as patient programmer 30 or clinician programmer 60. A clinician or patient 12 interacts with user interface 106 in order to manually change the stimulation parameters of a program, change programs within a group, turn posture responsive therapy ON or OFF, view therapy information, view posture state information, or otherwise communicate with IMD 14 or 26.

User interface 106 may include a screen and one or more input buttons, as in the example of patient programmer 30, that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Input buttons for user interface 106 may include a touch pad, increase and decrease buttons, emergency shut off button, and other buttons needed to control the stimulation therapy, as described above with regard to patient programmer 30. Processor 104 controls user interface 106, retrieves data from memory 108 and stores data within memory 108. Processor 104 also controls the transmission of data through telemetry module 110 to IMD 14 or 26. Memory 108 includes operation instructions for processor 104 and data related to patient 12 therapy.

Telemetry module 110 allows the transfer of data to and from IMD 14, or IMD 26. Telemetry module 110 may communicate automatically with IMD 14 at a scheduled time or when the telemetry module detects the proximity of the stimulator. Alternatively, telemetry module 110 may communicate with IMD 14 when signaled by a user through user interface 106. To support RF communication, telemetry module 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Figure 7:
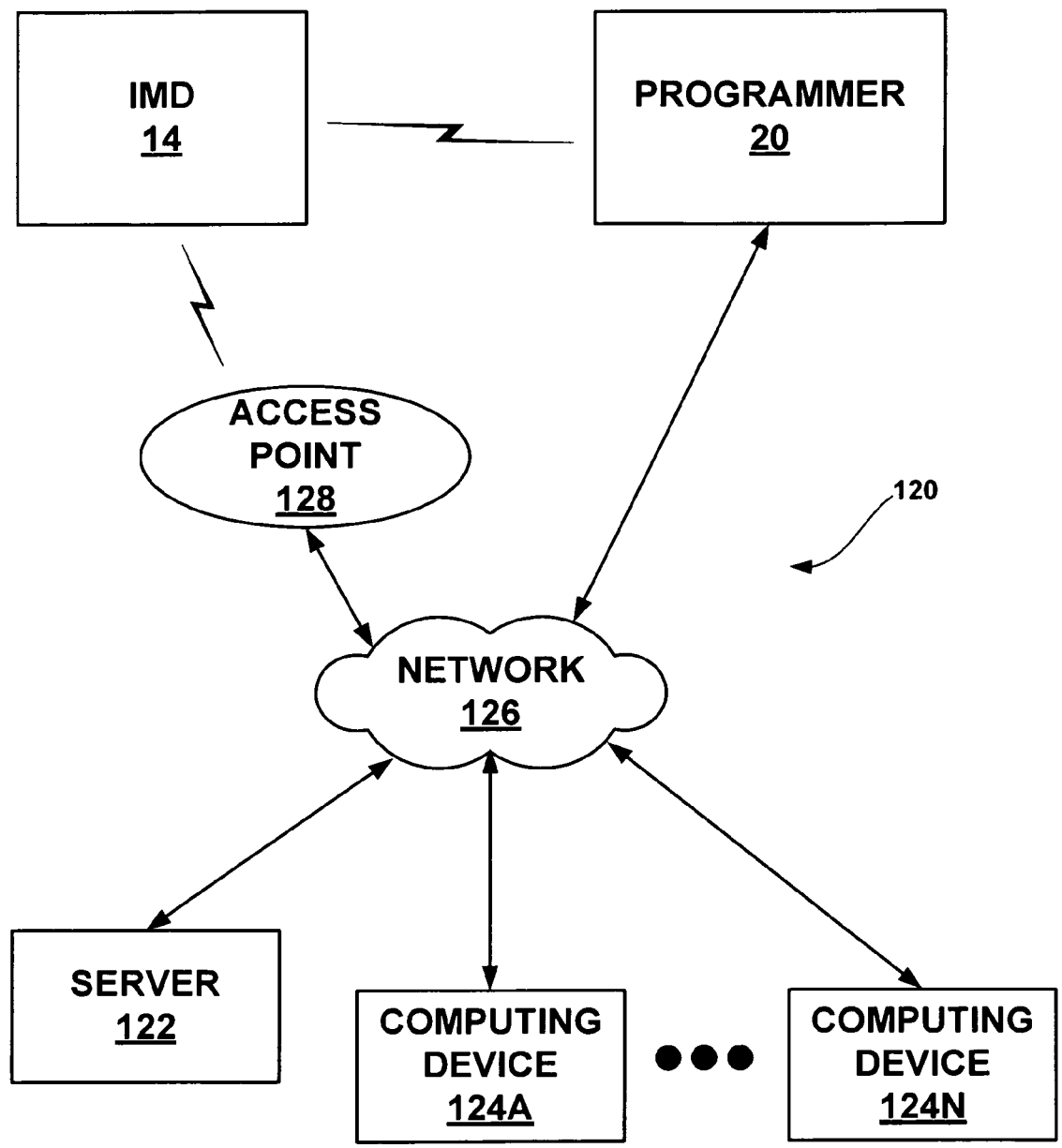
FIG. 7 is a block diagram illustrating an example system that includes an external device, such as a server, and one or more computing devices that are coupled to an implantable medical device and external programmer shown in FIGS. 1A-1C via a network.

Dwell time analysis, posture state detection, therapy adjustment, dwell time adjustment and other functions may be performed in IMD 14 or in programmer 20 or a combination of both in various example implementations. Also, in some instances, as illustrated by FIG. 7 below, such operations could be performed by one or more remote devices. Using telemetry, IMD 14 and programmer 20 may exchange information such that various operations may be performed in IMD 14 or programmer 20 or distributed between the two devices. For purposes of illustrations, application of dwell time analysis and adjustment will be described with respect to IMD 14, without limitation as to performance of some or all of such processes within programmer 20 or another device. External programmer 20 may be either patient programmer 30 or clinician programmer 60.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry module 88 to communicate with external programmer 20 via a first wireless connection, and to communicate with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, digital signal processors (DSPs), application specific integrated circuits (ASICs), field programmable gate arrays (FPGAs), programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other examples, access point 128 may be coupled to network 126 through different forms of connections, including wired or wireless connections.

During operation, IMD 14 may collect and store various forms of data. For example, IMD 14 may collect sensed posture state information during therapy delivery that indicate how patient 12 moves throughout each day. In some cases, IMD 14 may directly analyze the collected data to evaluate the posture state of patient 12, such as what percentage of time patient 12 was in each identified posture state. In other cases, however, IMD 14 may send stored data relating to posture state information to external programmer 20 and/or server 122, either wirelessly or via access point 128 and network 126, for remote processing and analysis. For example, IMD 14 may sense, process, trend and evaluate the sensed posture state information. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components.

Figure 8A:
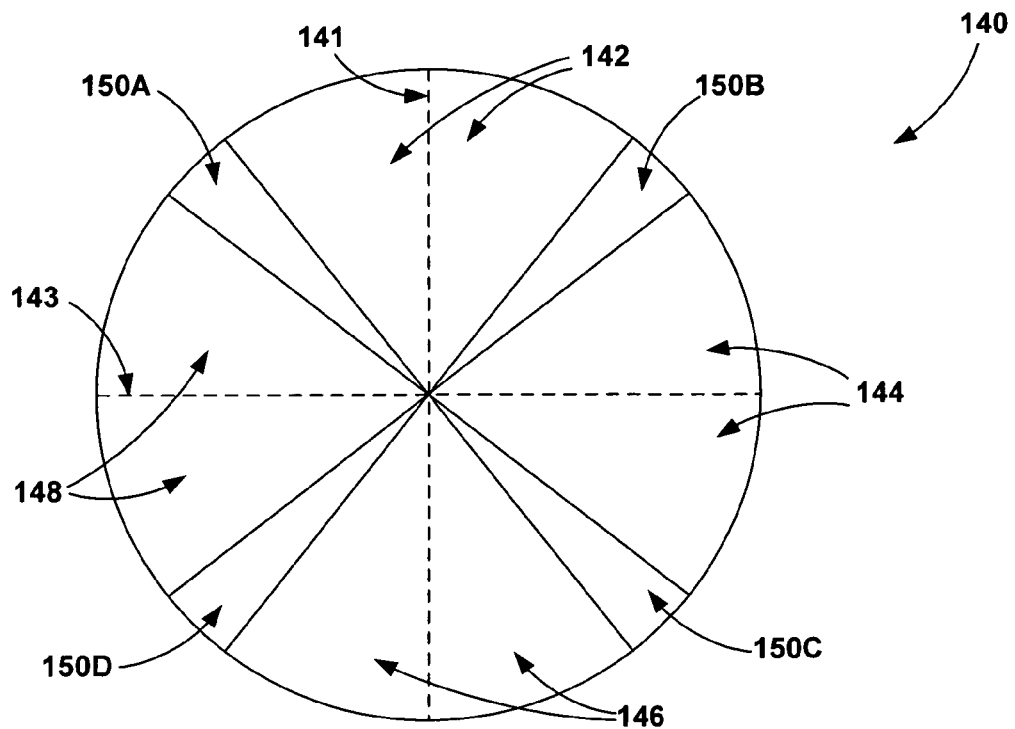
FIGS. 8A-8C are conceptual illustrations of posture volumes and vectors that may be used to define a posture state of a patient based on signals sensed by a posture state sensor.
Figure 8B:
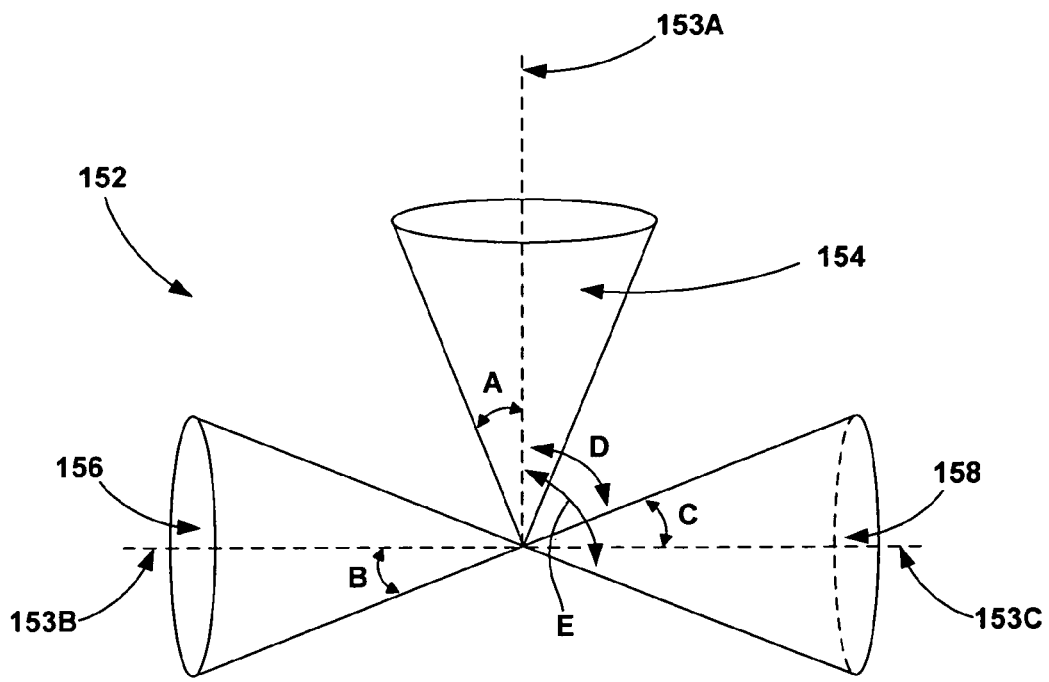
Figure 8C:
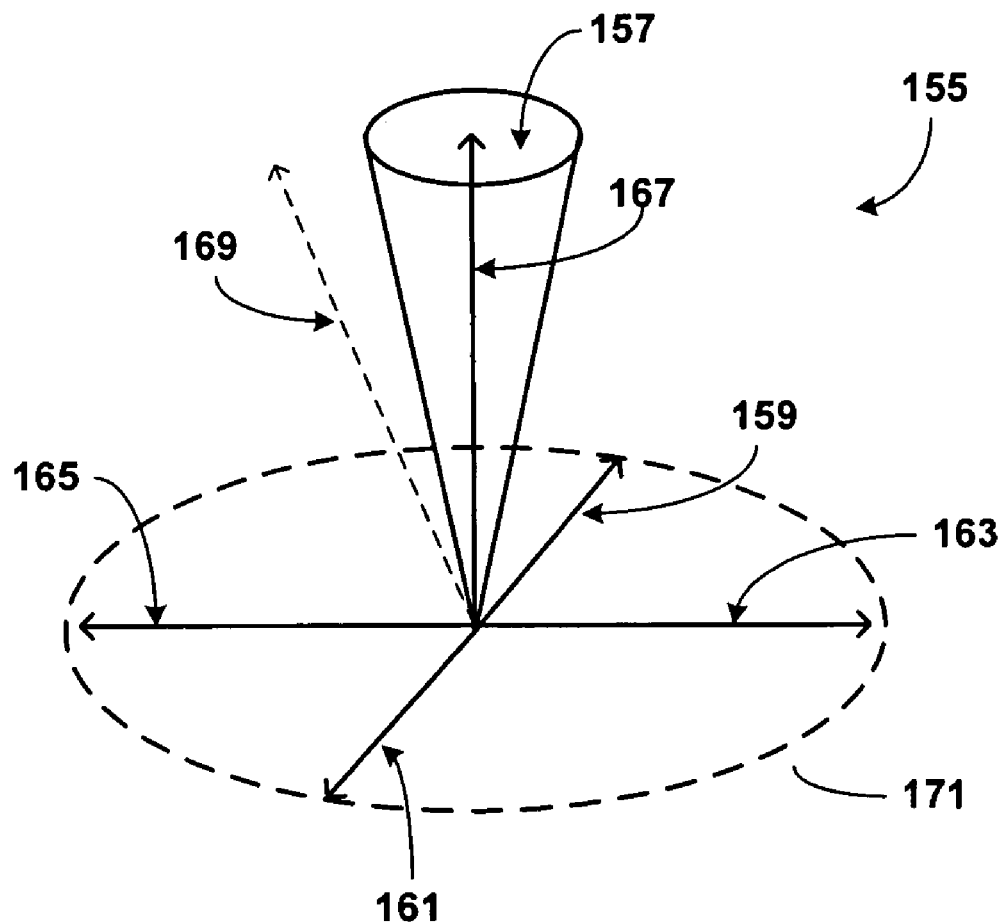

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up (lying back) cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down (lying front) cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, example posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some examples, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E" may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinate vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, e.g., as described above with respect to the description of posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate cones 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

A posture state definition may also include an activity component, e.g., an activity level, in addition to a posture component, e.g., a posture cone. For example, an "upright active" posture state may be defined by upright posture cone 154 in combination with a "medium" or "high" activity level. Whereas, the "upright" posture state may be defined by upright posture cone 154 in combination with a "low" activity level. As described previously, other gradations, e.g., high, medium high, medium, medium low, and low, or numerical scales may be used to characterize activity level.

As may be appreciated, patient 12 will occupy different posture states as he goes about daily life. For instance, when patient 12 is in an upright position such that the posture state parameter value lies within upright posture cone 154, posture state module 86 will detect the patient's posture state as upright. If patient 12 transitions from the upright position to lying on his back, the detected posture state parameter value will transition from being located within upright cone 154 into the space that is not associated with any posture state definition. From there, the detected posture state parameter value will transition into lying back cone 156, which indicates that patient 12 is lying on his back.

According to the current example, patient 12 may be receiving some therapy associated with the upright posture state while the detected posture state parameter value resides within upright cone 154. This therapy may optionally continue as the posture state parameter value enters the space that is not associated with any defined posture state or some other therapy may be delivered during this time. In one example, some change in therapy may be initiated as the detected posture state parameter value enters lying back cone 156, which indicate that patient 12 is lying on his back. Thus, a change in therapy may be initiated as the patient's posture state is reclassified. Alternatively or additionally, some other action may be taken as a result of this posture state reclassification.

As previously discussed, a dwell time may be imposed between the time the patient's posture state is reclassified from a previous posture state to a newly detected posture state and the time a response is initiated as a result of this reclassification. This dwell time may, if desired, be programmable, and may be different for different posture states or different posture state transitions. In one example, the dwell time may be selected based on the patient's previous posture state classification (in this example, the upright posture state). In another example, the dwell time may be selected based on the newly-assumed posture state (in this example, the lying back posture state). In yet another example, this dwell time may be selected based on the particular posture state transition (e.g., upright to lying back) that was experienced by patient 12. According to another aspect, the dwell times may further be specific to a particular type of response or action that is to be initiated, such as therapy adjustment of notification of posture change.

The use of dwell time may serve to stabilize the system by ensuring that transient, temporarily-assumed posture states do not prompt a therapy adjustment or other response. If the detected posture state is only transitory, as may be the case if patient 12 is transitioning to a final posture state by assuming one or more temporary posture states, the temporarily-assumed posture states will not cause delivered therapy to be adjusted in an unwanted or premature manner. Moreover, if patient 12 aborts a posture state transition, as by changing his mind mid-way through the transition, the aborted transition likewise will not prompt a therapy change if the dwell time is not exceeded while the patient is in the transient posture state. Instead, the therapy is not adjusted and continues to be delivered in a manner appropriate for the previous stable posture.

If desired, a dwell time may be selected that is specific to a particular response. As an example, upon entry of the lying back posture state, more than one response may be initiated. One such response may involve adjustment of a therapy parameter, e.g., an increase or decrease of an amplitude used to deliver stimulation therapy. Another response may involve initiation of a different therapy, e.g., initiation of administration of a therapeutic substance to patient 12. Yet another response may involve providing some type of notification to external programmer 20, e.g., patient programmer 30 or clinician programmer 60. For each response that is to occur as a result of the newly-detected posture state, a different dwell time may be imposed. Thus, dwell times, if desired, may be posture state-specific, posture state transition-specific, and/or response-specific.

While patient 12 resides in a given posture state or transitions between posture states, he may make therapy adjustments, e.g., manually via patient programmer 30. In some cases, patient 12 may make therapy adjustments relative to therapy delivered automatically by IMD 14 based on posture state detection. Hence, patient 12 may manually override some automated therapy parameter settings in some instances. Patient therapy adjustments may indicate that automated therapy parameter settings are not appropriate for patient 12 in a given posture state, or that it may be desirable to adjust the automated therapy parameter settings in order to improve therapeutic efficacy. A clinician may analyze patient therapy adjustment data to adjust therapy parameter settings for various posture states. Alternatively, or additionally, IMD 14 may be configured to automatically adjust therapy based on patient therapy adjustment data.

In addition to indicating whether automated therapy settings are appropriate, patient therapy adjustments may provide an indication that dwell times are too short or too long. In this case, it may be desirable to adjust the dwell time based on patient therapy adjustment data. To help ensure that the dwell time is set to an appropriate length of time, patient therapy adjustment data may be recorded and analyzed by IMD 14 and/or programmer 20 (which may be a patient programmer 30 or clinician programmer 60). Therapy adjustments made by the patient during the dwell time may indicate that the dwell time is too long. Likewise, therapy adjustments made by the patient after expiration of the dwell time may indicate that the dwell time is too short. Based on analysis of the patient therapy adjustment data, the dwell time can be adjusted by IMD 14, programmer 20, or a user such as a clinician. In particular, the dwell time can be adjusted to a length of time that is appropriate for the patient and/or posture state.

To help ensure that the dwell time is set to an appropriate length of time, IMD 14 and/or programmer 20 may record and analyze therapy adjustment data indicating therapy adjustments may by a user, such as a patient. The therapy adjustments may be manual therapy adjustments entered by a user via programmer 30. The therapy adjustment data may indicate the timing of the therapy adjustments relative to dwell time and detected posture states, the parameters that were adjusted, the parameter values selected by the user, and other pertinent therapy adjustment information.

The therapy adjustment data may be analyzed automatically by IMD 14 and/or programmer 20 to determine whether the dwell time should be adjusted. If so, IMD 14 and/or programmer 20 may automatically adjust the dwell time. In other examples, IMD 14 and/or programmer 20 may store patient therapy adjustment data for analysis by a clinician. The clinician then may consider adjustments to dwell time or dwell times based on the therapy adjustment data.

In some cases, the patient therapy adjustment data may be collected and stored by IMD 14 and/or programmer 20 during a therapy session in which IMD 14 delivers therapy to patient 12, between successive programming sessions. IMD 14 and/or programmer 20 may automatically adjust dwell time during a therapy session. Alternatively, a clinician may analyzed the patient therapy adjustment data during the next programming session, e.g., in-clinic, and adjust the programming of IMD 14 to apply adjusted dwell time or dwell times in the next therapy session.

A therapy adjustment that is entered after the detection of a newly detected posture state but before expiration of the dwell time may indicate that patient 12 would like IMD 14 to transition more quickly to particular therapy setting upon reaching the new posture state. For example, patient 12 may experience lack of pain coverage or other discomfort if IMD 14 does not deliver a therapy adjustment until expiration of a prolonged dwell time. Instead, patient 12 may desire that the therapy adjustment be delivered more quickly upon detection of the new posture state. In this case, based on therapy adjustment data, IMD 14, programmer 20 or a user such as a clinician may determine that the pertinent dwell time is too long and should be shortened. By shortening the length of the dwell time, IMD 12 may respond more quickly to the detected posture state and thereby provide the therapy adjustment to patient 12 more quickly upon assuming the detected posture state.

As another illustration, if the therapy adjustment data indicates that the patient adjusted therapy following detection of a posture state and after expiration of the dwell time, and the adjustment tends to return close to or toward the therapy delivered for the previous posture state, IMD 14, programmer 20 or a clinician may determine that the patient is not yet in need of the therapy adjustment for the newly detected posture state. For example, if patient 12 does begin to feel adverse effects on efficacy until some period of time after a posture state has stabilized, i.e., until some time after the dwell time, the patient may seek to return to the previous therapy setting, which may have been comfortable for the previous stable posture.

Until the time that patient 12 begins to feel adverse effects produced by the new posture, the patient may feel more comfortable with the previous therapy parameters delivered for the previous posture state. Based on analysis of the therapy adjustment data, IMD 14, programmer 20 or a clinician may determine that the length of the dwell time should be increased. In some cases, a therapy adjustment made after expiration of the dwell time may be evaluated to determine whether it is consistent with a return close to or toward the therapy delivered for the previous stable posture as additional confirmation that it may be desirable to lengthen the dwell time.

In general, IMD 14, programmer 20, or a combination of both may perform a method comprising delivering therapy to a patient, and detecting a posture state transition of a patient. Upon expiration of a dwell time for the posture state transition, IMD 14 and/or programmer 20 may adjust the therapy based on the posture state transition, detect a patient adjustment of the therapy, and adjust the dwell time if the patient adjustment is detected during or after the dwell time. As will be described, the dwell time may be adjusted if a number of patient adjustments detected during multiple instances of the posture state transition exceeds a threshold. The dwell time may be reduced based on patient adjustment timing if the patient adjustment is detected during the dwell time, or increased based on patient adjustment timing if the patient therapy adjustment is detected after the dwell time.

In some cases, IMD 14 and/or programmer 20 may determine whether the patient adjustment is consistent with the adjustment of therapy based on the posture state transition, and adjust the dwell time if the patient adjustment is detected during or after the dwell time and the patient adjustment is consistent with the adjustment of therapy based on the posture state transition. Therapy may be adjusted based on a plurality of different posture state transitions upon expiration of dwell times for the respective posture state transitions, where at least some of the dwell times are different for different posture state transitions. In this case, adjusting the dwell time may include adjusting different dwell times for different posture state transitions based on patient therapy adjustments detected during or after the respective dwell times.

Figure 9A:
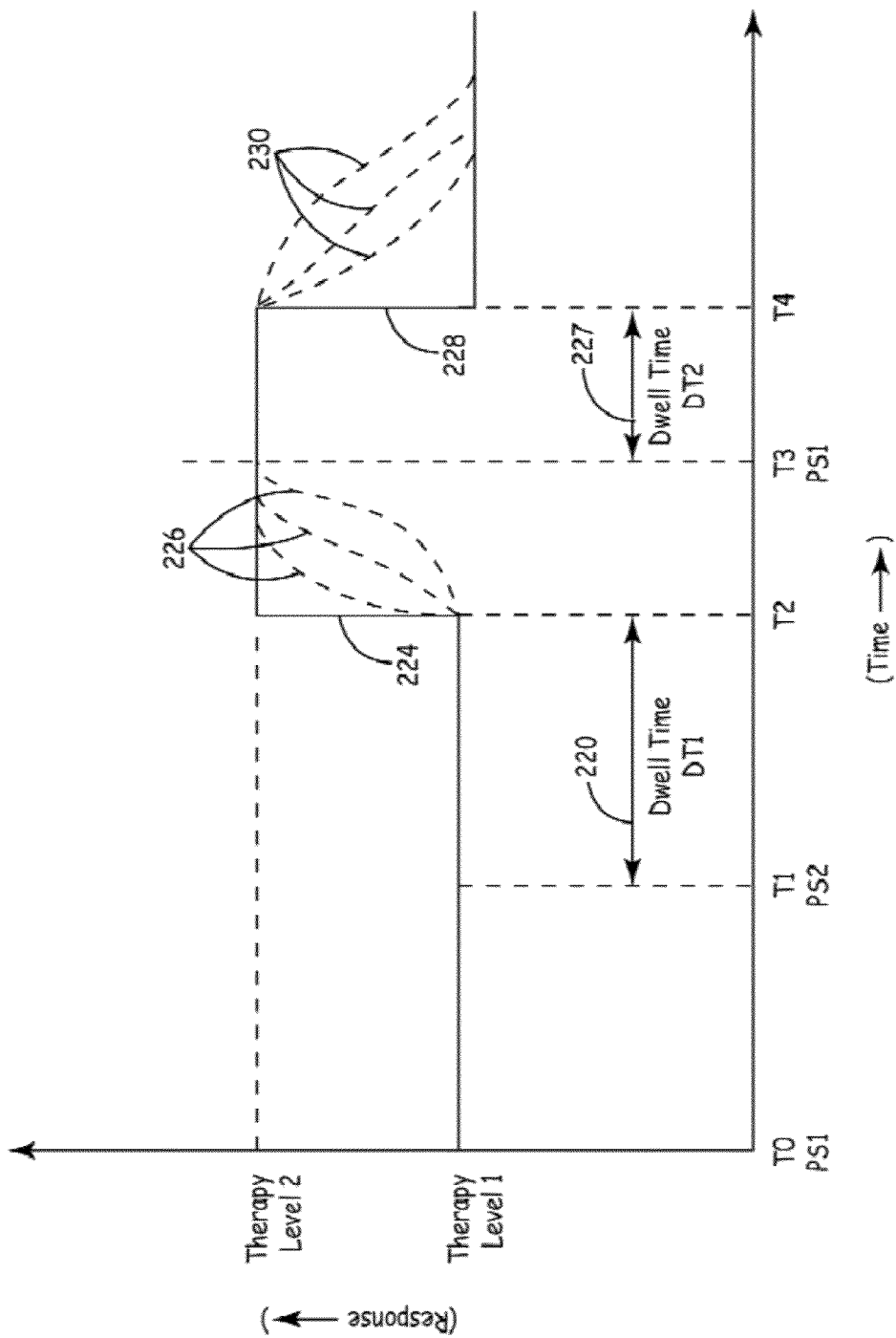
FIG. 9A is a timing diagram illustrating use of dwell times according to one aspect of the disclosure.

FIG. 9A is a timing diagram illustrating use of dwell times according to one example. This diagram illustrates using detection of posture states to control delivery of therapy, although such detection may be used for initiating other responses, such as notification or data storage, as discussed above. At time T0, it will be assumed that a first stable posture state has already been detected and is being used as the basis for delivery of therapy with a first set of therapy parameters. In particular, IMD 14 delivers therapy with therapy parameters that have been specified for the particular posture state, or perhaps a group of posture states. In the example of FIG. 9A, the therapy will be described in terms of a adjustment of therapy amplitude, referred to as a therapy level, although other therapy adjustments may be made.

As shown in FIG. 9A, IMD 14 delivers the therapy at a first therapy level, Therapy Level 1, which has been associated with posture state PS1. At time T1, a second, different posture state PS2 is detected. It will be assumed that a different therapy level, Therapy Level 2, has previously been associated with this posture state PS2. Rather than immediately change the therapy level to Therapy Level 2 in response to detection of posture state PS2, a dwell time is imposed. In particular, a timer/counter, which may be referred to as a "dwell timer," is started for a dwell time DT1 that has been associated with this posture state change. Different dwell times may be used for different posture states or posture state transitions, or the same dwell time could be use for all posture states and posture state transitions.

As previously discussed, many possibilities exist for selecting which dwell time will be used in a given situation. In a simple example, one dwell time may be used for all posture state changes. In a more complex system, the dwell time may be selected based on the particular posture state change or transition that is occurring (e.g., upright to lying front, lying front to lying back, or the like), based on the most-recent stable posture state, based on the newly-detected posture state, based on a response type (e.g., therapy adjustment, notification, or data storage), and/or based on some other monitored condition.

For instance, the dwell time DT1 may be selected based on the previous stable posture state PS1 that was assumed by patient 12 prior to the most recent posture state transition. Alternatively, the dwell time DT1 may instead be selected based on the newly-detected posture PS2. In another example, the specific transition from PS1 to PS2 may be used to select the dwell time. Other system conditions, such as physiological conditions of patient 12, e.g., heart rate or blood pressure, may be used to select dwell time.

In the current example of FIG. 9A, dwell time DT1 expires at time T2, as indicated by arrow 220. Since the patient's posture state did not change throughout the dwell time, upon expiration of this dwell time, the level of therapy delivery is changed from Therapy Level 1, which is associated with PS1, to Therapy Level 2, which is associated with PS2. This change may occur as a single step function, as shown by step function 224. However, in another example, the change will occur over time, such as using a ramp or some other therapy adjustment function by which the therapy level changes somewhat gradually in a series of small steps or a continuous change. For more gradual adjustment, any type of linear or non-linear ramp or exponential attack function may be used, as shown by dashed lines 226, to achieve the target Therapy Level 2. The type of ramp or attack function used in the system and/or the time over which the change to the second therapy level occurs may be programmable.

At time T3, the patient's posture state again reverts to posture state PS1. Rather than immediately revert back to Therapy Level 1, a dwell time is imposed. In this example, the dwell time selected for this situation, dwell time DT2, is different than the time DT1 used when patient 12 entered posture state PS2. This selected dwell time, which is represented by arrow 227, may be based on any of the considerations discussed above. Alternatively, a universal dwell time may be employed for use when any posture transition is detected, as previously mentioned.

As with the case discussed above, dwell time DT2 expires at time T4 without patient 12 shifting posture states. Therefore, the therapy level associated with PS1 is again delivered to patient 12. This reversion to Therapy Level 1 is shown to occur as a step function 228. However, any type of linear ramp or decay function may be selected instead, as shown by dashed lines 230. The function selected to respond to a decrease in therapy level may be different than the function selected to respond to an increase in therapy level. That is, if desired, the one of functions 226 that is selected in response to a therapy increase is not required to correspond to the one of functions 230 that is selected in response to a therapy decrease. In the foregoing manner, dwell times may be imposed between the time a shift in posture state is detected and the time a response, which in this case is a therapy level adjustment, is initiated.

Figure 9B:
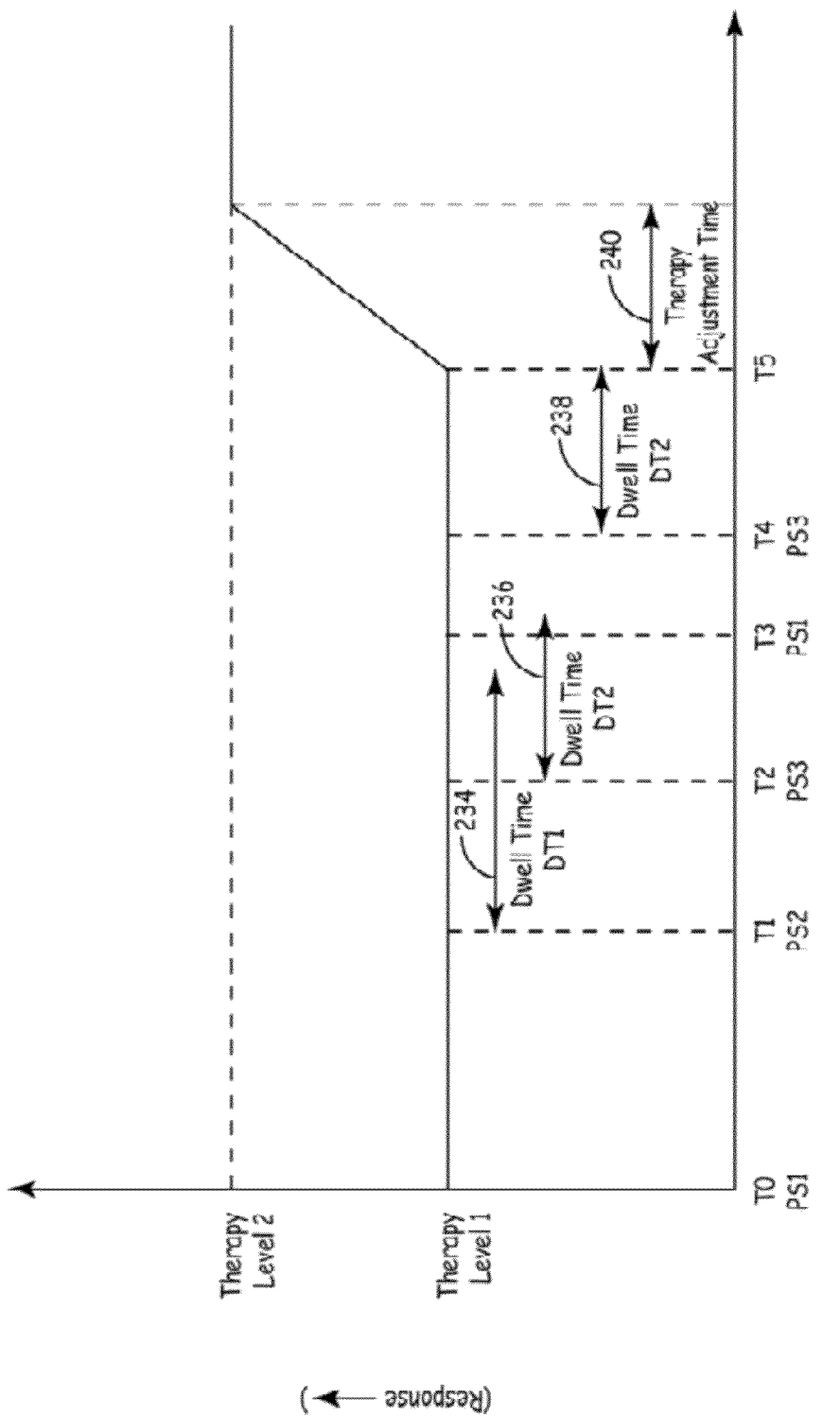
FIG. 9B is a timing diagram illustrating use of dwell times according to another aspect of the disclosure.

FIG. 9B is a timing diagram illustrating use of dwell times according to another example of the disclosure. This timing diagram, like the one discussed in regards to FIG. 9A, depicts delivery of therapy at various therapy levels. These therapy levels are delivered in response to detected posture states. At time T0, in FIG. 9B, a posture state PS1 has already been detected and is being used to deliver therapy for that posture state PS1 at Therapy Level 1. At time T1, a second, different posture state PS2 is detected. As was the case in the foregoing example, a different Therapy Level 2 is associated with this posture state. Rather than immediately change the therapy level to Therapy Level 2 in response to detection of posture state PS2, a dwell time DT1 is imposed, as shown by arrow 234.

At time T2, before this dwell time DT1 expires, the patient's posture state changes again to a third posture state PS3, which is different from the original posture state PS1. Therefore, the timer associated with DT1 is reset, and a timer is started for this third posture state PS3, as indicated by arrow 236. The dwell time associated with this timer, DT2, is different from the dwell time DT1 used for PS2, although this need not be the case in other examples.

At time T3, the patient's posture again shifts back to the original posture PS1. Since this occurs prior to expiration of dwell time DT2, as may be seen by arrow 236, the dwell timer that was started upon the patient's classification in posture state PS3 is reset. Once again, no therapy change occurs because the applicable dwell time has not expired. In this case, therapy is still being delivered at Therapy level 1, which is the therapy level associated with PS1. No dwell timer needs to be started, since therapy is already being delivered at the level associated with this newly-assumed posture state of PS1.

At time T4, patient 12 assumes posture state PS3 again. Therefore, a dwell timer is started to time dwell time DT2, as shown by arrow 238. At time T5, the dwell timer expires while patient 12 is still assuming posture state PS3. Therefore, the associated response is initiated, which in this example, is an adjustment in therapy to Therapy Level 2. As was the case in FIG. 9A, the therapy adjustment may be initiated as a step function. However, in one example, the change will occur over time, as a ramp or some other therapy adjustment function, such as an exponential ramp function. The current example of FIG. 9B shows the change in therapy occurring as a ramp function, with an increase to the target Therapy Level 2 achieved over a therapy adjustment time indicated by arrow 240, which in one example may be programmable. Although the therapy adjustment in FIG. 9B is depicted as an increase in therapy level for purposes of illustration, the therapy adjustment could be a decrease in therapy level, depending on the difference in therapy level for posture state PS1 and posture state PS3.

The foregoing examples of FIGS. 9A and 9B assume that dwell times will be automatically selected based on the newly-assumed postures. For instance, in FIG. 9B, dwell time DT1 is used for newly-assumed posture state PS2, whereas dwell time DT2 is used for newly-assumed posture state PS3. In another example, the previously-detected stable posture state could be used for this purpose. For instance, in FIG. 9B, a dwell time associated with posture state PS1 (rather than new posture state PS2) could be selected for use after the re-classification of patient 12 in posture state PS2 at time T1. Accordingly, dwell times may be selected in a variety of ways.

Figure 9C:
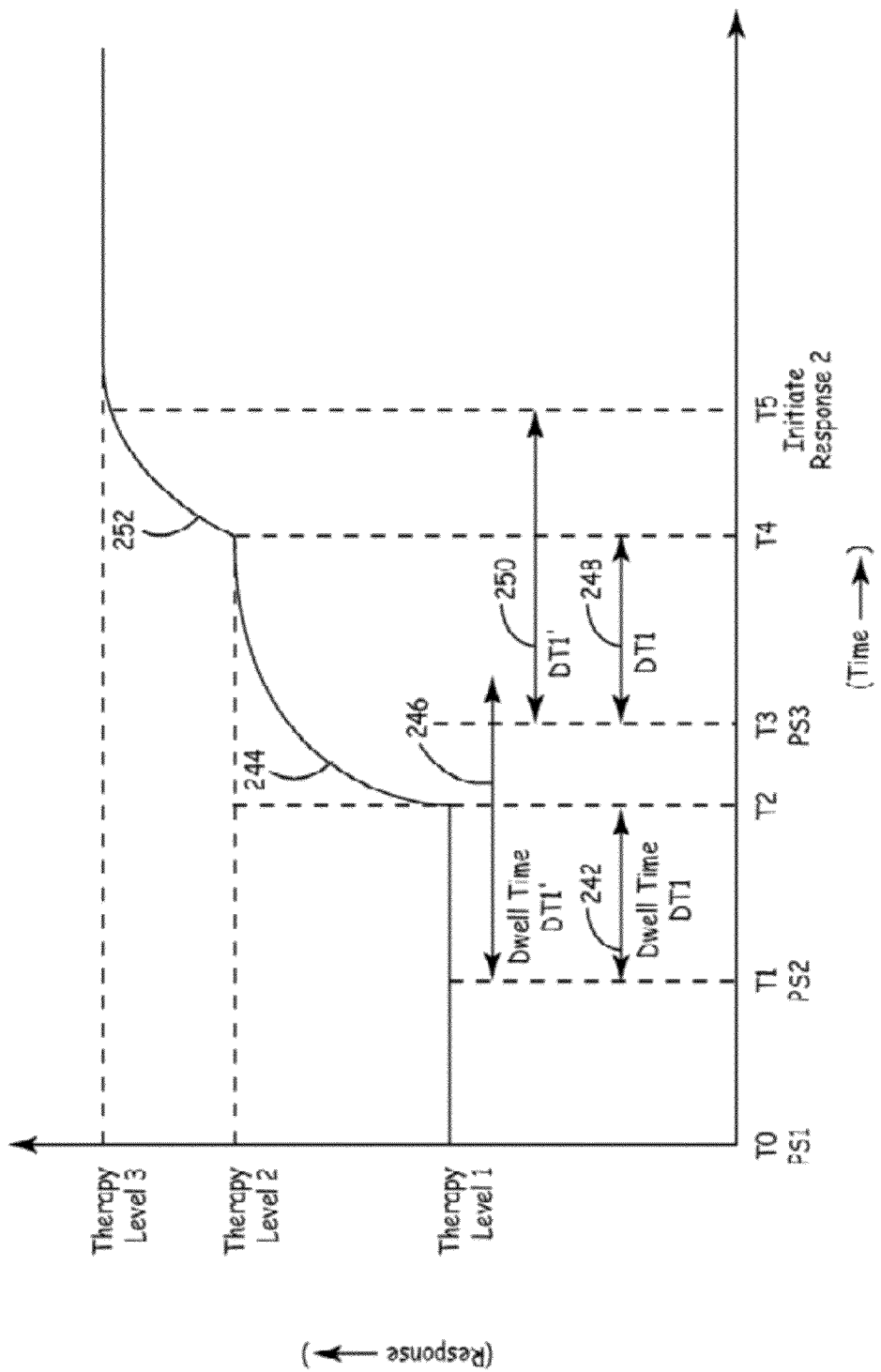
FIG. 9C is a timing diagram illustrating use of dwell times according to yet another aspect of the disclosure.

FIG. 9C is a timing diagram illustrating use of dwell times according to yet another example of the disclosure. This diagram describes use of multiple dwell times in response to a single detected posture state change. These dwell times are used to initiate multiple responses. At time T0, it is assumed that patient 12 has been classified in a stable posture state PS1 and a therapy level associated with this posture state, Therapy Level 1, is being used to deliver therapy to patient 12. At time T1, patient 12 is classified in a second, different posture state PS2. It will be assumed that a different Therapy Level 2 is associated with this posture state. Rather than immediately change the therapy level to Therapy Level 2 in response to re-classification of the patient's posture state, a dwell time DT1 is imposed. In particular, a timer is started for a dwell time DT1 that has been associated with this posture state change and that will be used to initiate a change in therapy level. This dwell time DT1 is represented by arrow 242.

In addition, in this example, a second timer is started that is associated with a different dwell time DT1' that is longer than the dwell time DT1, as indicated by arrow 246. This second time will be used to initiate a response other than the change in therapy level. For instance, this other dwell time DT1' may be used to change the level of some therapy other than that represented by FIG. 9C, to start another therapy, stop another therapy, initiate a notification, prompt storing of data, start a communication session, or initiate some other response. In this example, therapy adjustment may be initiated upon expiration of dwell time DT1, but the other response is initiated later, upon expiration of dwell time DT1'.

At time T2, the first dwell timer associated with dwell time DT1 expires, as shown by arrow 242. Therefore, the therapy level is changed to Therapy Level 2. This change is not immediate in this example, but rather occurs according to an exponential attack function, as shown by curve 244. At time T3, before the second dwell timer associated with dwell time DT1' expires, patient 12 changes his posture state to PS3. Thus, this second dwell timer is reset, and the response associated with this second timer is not initiated. Instead, at least one timer associated with posture state PS3 is started. In this example, a first dwell timer is started for a dwell time DT1, as shown by arrow 248. This dwell timer will be associated with a change in therapy to a level that is associated with PS3. A second dwell timer is also started in response to this change to posture state PS3 that will be used to initiate a second response. This second dwell timer will expire after the dwell time DT1', as indicated by arrow 250.

At time T4, the first dwell timer associated with time DT1 expires, and therapy levels are therefore adjusted to levels associated with posture state PS3, which in this example will be assumed to be Therapy Level 3. As was the case with Therapy Level 2, the change does not occur immediately, but occurs using an exponential attack function shown by curve 252. At time T5, the second dwell timer associated with DT1' also expires, resulting in initiation of the second response, which may be any one of a number of responses associated with this shift to posture state 3.

In this example, the dwell times that are selected are the same for both posture changes. That is, when the posture change to PS2 occurs at time T1, the dwell time DT1 is selected for use in initiating a change in therapy level, and the dwell time DT1' is selected for use in initiating a second response. These same two dwell times are also selected for use when the shift to posture state PS3 occurs. Thus, this example shows that the dwell times may be response-specific, and not based on the posture states being assumed. Of course, the same dwell time may be used to initiate multiple responses in another example. In still another example, the selected dwell time may be both response-specific, and also based on posture state information (e.g., most-recent stable posture state, newly-assumed posture state, transition between the two, and so forth.)

It may be appreciated that FIGS. 9A-9C are merely examples, and that many other scenarios may be contemplated for using one or more dwell times to control initiation of therapy adjustments and one or more additional responses as a result of one or more posture state changes.

Figure 10:
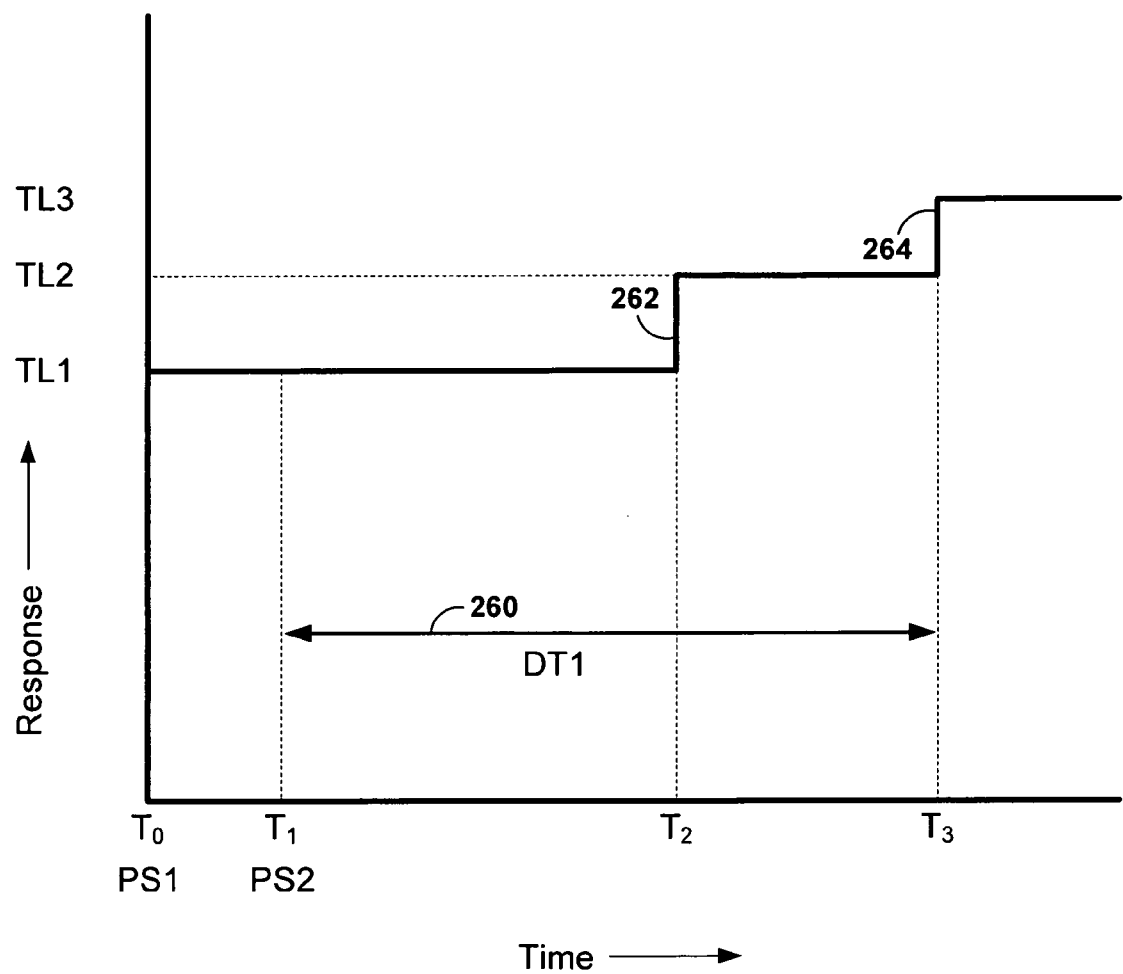
FIG. 10 is an example timing diagram illustrating a manual therapy adjustment prior to expiration of the dwell time.

FIG. 10 is an example timing diagram illustrating a manual therapy adjustment prior to expiration of the dwell time. At time T0, it will be assumed that a first stable posture state has already been detected and is being used to control therapy delivery at a first therapy level, therapy level TL1, which has been associated with posture state PS1. At time T1, a second, different posture state PS2 is detected. It will be assumed that a different therapy level, therapy level TL3, has previously been associated with this posture state PS2. Rather than immediately change the therapy level to therapy level TL3 in response to detection of posture state PS2, a dwell time is imposed. In particular, a timer/counter, which may be referred to as a "dwell timer," is started for a dwell time DT1 that has been associated with this posture state change.

As previously discussed, many possibilities exist for selecting which dwell time will be used in a given situation. In a simple example, one dwell time may be used for all posture state changes. In a more complex system, the dwell time may be selected on the particular posture state change that is occurring, on the most-recent stable posture state, on the newly-detected posture state, on a response type, and/or on some other monitored condition. For instance, the dwell time DT1 may be selected based on the previous stable posture state PS1 that was assumed by patient 12 prior to the most recent posture state transition. Alternatively, the dwell time DT1 may instead be selected based on the newly-detected posture PS2. In another example, the specific transition from PS1 to PS2 may be used to select the dwell time. Other system conditions, such as physiological conditions of patient 12, e.g., heart rate or blood pressure, may be used to select dwell time. In the current example, dwell time DT1 expires at time T3, as indicated by arrow 260.

At time T2, prior to expiration of dwell time DT1, the level of therapy delivery changes from therapy level TL1 to therapy level TL2. This change may occur in response to a manual therapy adjustment received from a user, e.g., via external programmer 20. The therapy adjustment may be manual in the sense that the adjustment occurs in response to user input rather than based on a therapy level previously associated with the new posture state, PS2. Manual changes may generally encompass any changes based on user input, including input based on manipulation of buttons, touchscreen media, or other media such as voice recognition.

The change from therapy level TL1 to therapy level TL2 in the example of FIG. 10 may occur as a step function, as shown by step function 262. However, in another example, the change may occur over time, such as using a ramp or some other therapy adjustment function. For example, any type of linear or non-linear ramp or exponential attack function may be used to achieve the target therapy level TL2 in response to a manual therapy adjustment by a user such as patient 12. The type of ramp or attack function used in the system and/or the time over which the change to the second therapy level TL2 occurs may be programmable.

Additionally, since the patient's posture state did not change throughout dwell time DT1, upon expiration of this dwell time DT1, the level of therapy delivery is changed from the adjusted therapy level TL2 to therapy level TL3, which is associated with PS2. This change may occur as a step function, as shown by step function 224. However, as previously described, other types of transitions are also contemplated.

The user-initiated therapy adjustment at T2 may indicate that a shorter dwell time DT1 is preferred. For example, a user-initiated therapy adjustment that occurs during dwell time DT1 may indicate that patient 12 would prefer to receive the therapy associated with a newly assumed posture state, e.g., posture state PS2 in the example of FIG. 10, at an earlier time. In some examples, the therapy change received during dwell time DT1 may also be examined to determine if a shorter dwell time DT1 is preferred. The dwell time may be adjusted automatically by IMD 14 or programmer 20, or by a user such as a clinician.

As one example, if the process is implemented in IMD 14, processor 80 of IMD 14 may determine if the therapy adjustment received during dwell time DT1 is consistent with a therapy change automatically initiated in response to the posture state transition from posture state PS1 to posture state PS2, i.e., the change from therapy level TL1 to therapy level TL3. Although processor 80 is primarily described herein for purposes of example, any suitable processor may perform the functions attributed to processor 80. For example, processor 92 of IMD 26 and/or processor 104 of external programmer 20 may perform some or all of the functions attributed to processor 80.

In the example of FIG. 10, the newly-assumed posture state PS2 is associated with a higher therapy level TL3 than the therapy level TL1 associated with the previous posture state PS1. Therefore, the therapy level may be automatically increased in response to the posture state transition from posture state PS1 to posture state PS2. Processor 80 may determine whether the therapy level TL2 associated with the user-initiated therapy adjustment received during dwell time DT1 is also higher than therapy level TL1 associated with posture state PS1. Processor 80 may also determine whether the therapy level TL2 associated with the user-initiated therapy adjustment received during dwell time DT1 is closer to the therapy level TL3 associated with the newly-assumed posture state PS2 than the therapy level TL1 associated with the previous posture state PS1.

If the therapy level TL2 associated with the user-initiated therapy adjustment received during dwell time DT1 is higher than therapy level TL1 associated with posture state PS1, processor 80 may determine that the therapy adjustment received during dwell time DT1 is consistent with the therapy change automatically initiated in response to the posture state transition from posture state PS1 to posture state PS2. In some examples, processor 80 may also compare therapy level TL2 associated with the user-initiated therapy adjustment to therapy level TL3 associated with the newly-assumed posture state PS2 to determine how closely the user-initiated therapy level matches the therapy level associated with the new posture state. For example, processor 80 may determine if therapy level TL2 associated with the user-initiated therapy adjustment is closer to therapy level TL3 associated with the newly-assumed posture state PS2 than therapy level TL1 associated with the previous posture state PS1.

If therapy level TL2 associated with the user-initiated therapy adjustment received during dwell time DT1 was lower than therapy level TL1 associated with posture state PS1, processor 80 may determine that the therapy adjustment received during dwell time DT1 is inconsistent with the therapy change automatically initiated in response to the posture state transition from posture state PS1 to posture state PS2. Processor 80 may also determine that the therapy adjustment received during dwell time DT1 is inconsistent with the therapy change automatically initiated in response to the posture state transition from posture state PS1 to posture state PS2 if therapy level TL2 associated with the user-initiated therapy adjustment is closer to therapy level TL1 associated with the previous posture state PS1 than therapy level TL3 associated with the newly-assumed posture state PS2. As a result, processor 80 may determine that the therapy adjustment received during dwell time DT1 does not indicate that a shorter dwell time DT1 is preferred. Instead, it may be determined that the therapy adjustment was an anomaly or that the therapy levels TL1 and TL3 may not be appropriate for the newly detected posture state.

If processor 80 determines that the user-initiated therapy adjustment is an indication that a shorter dwell time DT1 is preferred, processor 80 may automatically decrease dwell time DT1. For example, processor 80 may set dwell time DT1 to end at time T2 such that the new dwell time DT1 corresponds to the time between time T1 when patient 12 transitioned from posture state PS1 to posture state PS2 and time T2 when the user-initiated therapy change occurred. In other examples, processor 80 may use other techniques for decreasing dwell time DT1, e.g., decreasing dwell time DT1 by a specified percentage. Again, although processor 80 of IMD 14 is described for purposes of illustration, various aspects of the techniques described in this disclosure may be performed by IMD 14 or programmer 20 alone or in combination with one another.

Figure 11:
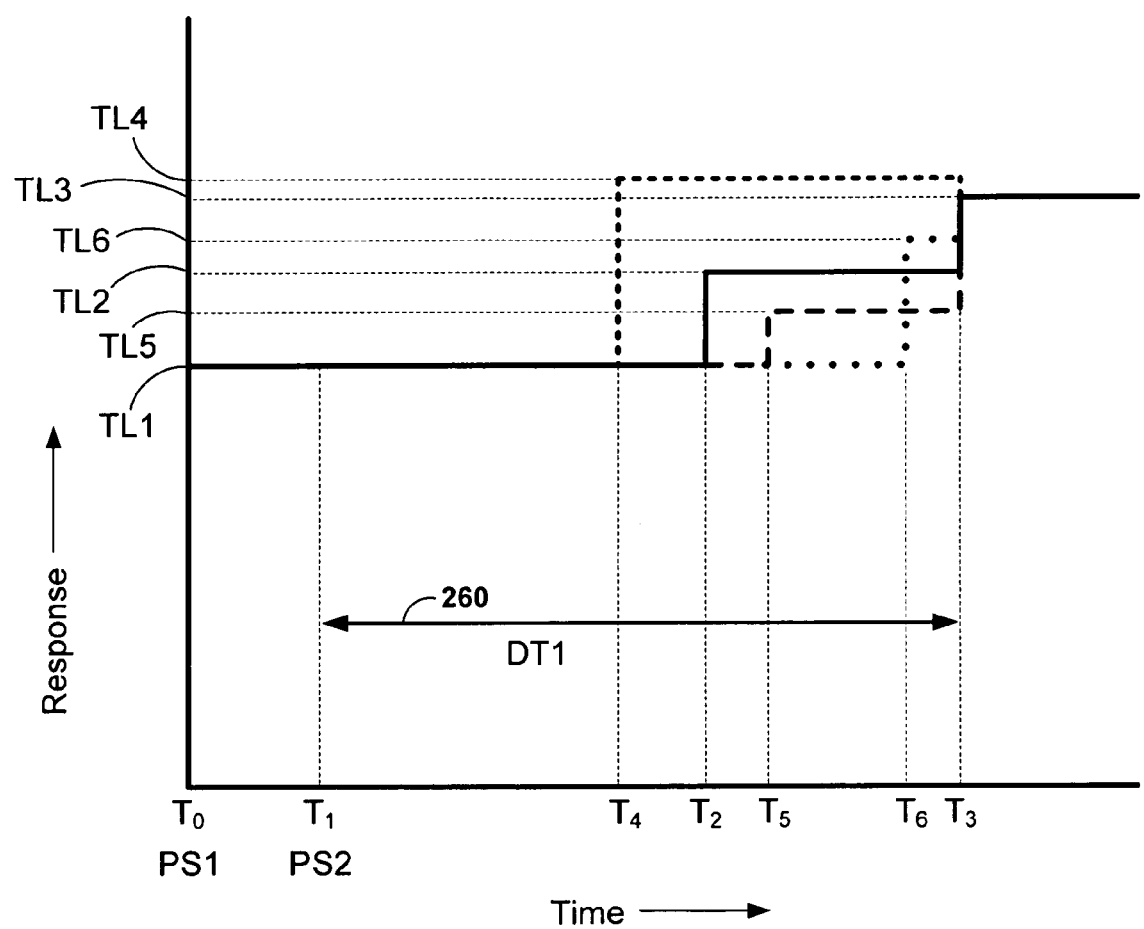
FIG. 11 is an example timing diagram illustrating a composite of user-initiated therapy adjustments recorded during various occurrences of the dwell time.

In some examples, processor 80 may monitor and record user-initiated therapy adjustments each time a dwell time is initiated in response to a posture state transition. FIG. 11 is an example timing diagram illustrating a composite of user-initiated therapy adjustments recorded during various occurrences of dwell time DT1. As previously described, many possibilities exist for selecting which dwell time will be used in a given situation. In the example of FIG. 11, dwell time DT1 may be specific to the particular posture state change that is occurring, i.e., the transition from posture state PS1 to posture state PS2. Although other techniques for selecting dwell time DT1 are also contemplated.

FIG. 11 is substantially similar to FIG. 10, but includes additional user-initiated therapy adjustments that occurred during other occurrences of dwell time DT1, i.e., after patient 12 transitioned from posture state PS1 to posture state PS2. As previously described, dwell time DT1 is initiated at time T1 in response to patient 12 transitioning from posture state PS1 to posture state PS2. Dwell time DT1 expires at time T3. Since, in the example illustrated in FIG. 11, patient 12 did not transition from posture state PS2 during dwell time DT1, therapy delivery according to therapy level TL3 associated with posture state PS2 is initiated at time T3.

At times T2, T4, T5, and T6, user-initiated therapy adjustments occurred. As illustrated in FIG. 11, each of therapy levels TL2, TL4, TL5, and TL6 corresponding to times T2, T4, T5, and T6, respectively, are higher than therapy level TL1. Therefore, each of these recorded therapy adjustments may be consistent with the automatic therapy increase from therapy level TL1 associated with posture state PS1 to therapy level TL3 associated with posture state PS2 expected when patient 12 transitions from posture state PS1 to posture state PS2. Each of times T2, T4, T5, and T6 and corresponding therapy levels TL2, TL4, TL5, and TL6 may indicate that patient 12 would prefer a shorter dwell time DT1. In other examples, processor 80 may examine how closely the adjusted therapy levels TL2, TL4, TL5, and TL6 match therapy level TL3 associated with newly assumed posture state PS3, e.g., whether each of therapy levels TL2, TL4, TL5, and TL6 is closer to therapy level TL1 associated with previous posture state PS1 or therapy level TL3 associated with newly-assumed posture state PS2, to determine whether each of the recorded therapy adjustments indicates that patient 12 would prefer a shorter dwell time DT1.

Processor 80 may determine a new decreased value for dwell time DT1 based on times T2, T4, T5, and T6 that user-initiated therapy adjustments occurred. As one example, processor 80 may average the time between time T1 at the start of the dwell time DT1 and each of times T2, T4, T5, and T6 corresponding to the recorded therapy adjustments to determine a new dwell time DT1. As another example, processor 80 may select the first time T2 that patient entered a therapy adjustment, and reduce the length of dwell time DT1 based on time T2, e.g., by reducing DT1 to be equal to T2−T1.

In the example of FIG. 11, posture state PS1 is associated with therapy level TL1 and posture state PS2 is associated with therapy level TL3 throughout each occurrence of the posture state transition from posture state PS1 to posture state PS2. In other examples, the therapy levels associated with posture states PS1 and PS2 may change over time, i.e., new therapy levels may be associated with posture states PS1 and PS2.

Figure 12:
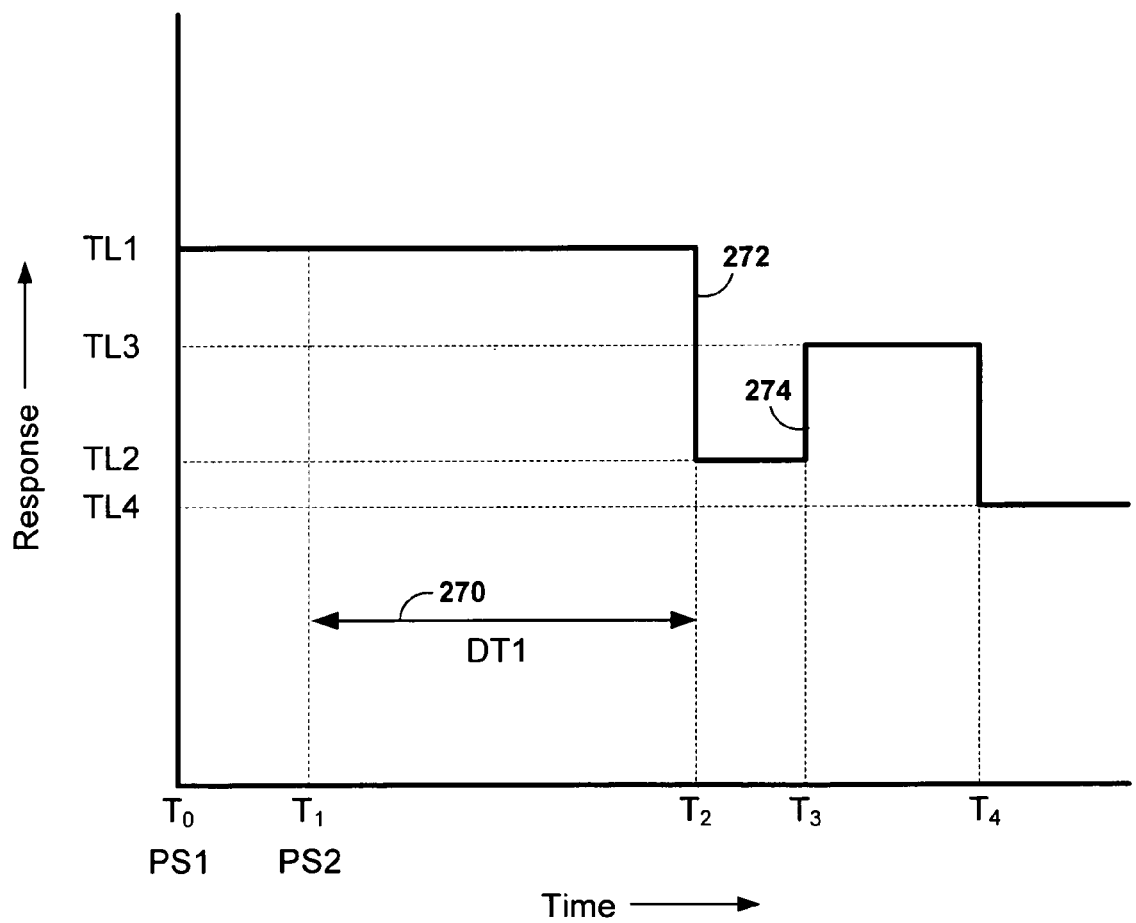
FIG. 12 is a timing diagram illustrating a manual therapy adjustment following expiration of a dwell time.

FIG. 12 is a timing diagram illustrating a manual therapy adjustment following expiration of a dwell time. At time T0, it will be assumed that a first stable posture state has already been detected and is being used to control therapy delivery at a first therapy level, therapy level TL1, which has been associated with posture state PS1. At time T1, a second, different posture state PS2 is detected. It will be assumed that a different therapy level, therapy level TL2, has previously been associated with this posture state PS2. Rather than immediately change the therapy level to therapy level TL2 in response to detection of posture state PS2, a dwell time is imposed. In particular, a timer/counter is started for a dwell time DT1 that has been associated with this posture state change.

In the current example, dwell time DT1 expires at time T2, as indicated by arrow 270. In response to the expiration of dwell time DT1, the level of therapy delivery automatically changes from therapy level TL1 associated with posture state PS1 to therapy level TL2 associated with posture state PS2, since patient 12 did not transition out of posture state PS2 during dwell time DT1 in the example of FIG. 12. This change from therapy level TL1 to therapy level TL2 may occur as a step function, as shown by step function 272. However, in another example, the change may occur over time, such as using a ramp or some other therapy adjustment function. For example, any type of linear or non-linear ramp or exponential decay function may be used to achieve the target therapy level TL2. The type of ramp or decay function used in the system and/or the time over which the change to the second therapy level TL2 occurs may be programmable.

At T3, following expiration of dwell time DT1, the level of therapy delivery changes from therapy level TL2 to therapy level TL3. This change may occur in response to a manual therapy adjustment received from a user, e.g., via external programmer 20. The therapy adjustment may be manual in the sense that the adjustment occurs in response to user input rather than automatically based on a therapy level previously associated with the new posture state, PS2. This change from therapy level TL2 to therapy level TL3 may occur as a step function, as shown by step function 274, although other types of transitions are also contemplated.

The user-initiated therapy change at T3 may indicate that a longer dwell time DT1 is preferred. For example, a user-initiated therapy change that occurs following dwell time DT1 may indicate that patient 12 would prefer to receive the therapy associated with the previous posture state, e.g., posture state PS1, for a longer period of time and transition to the therapy associated with a newly assumed posture state, e.g., posture state PS2, at a later time. In some examples, the therapy change received following dwell time DT1 may also be examined to determine if a longer dwell time DT1 is preferred.

Processor 80 of IMD 14 may determine if the therapy adjustment received following dwell time DT1 is consistent with changing the therapy in the direction of therapy level TL1 associated with previous posture state PS1. In the example of FIG. 12, the previous posture state PS1 is associated with a higher therapy level TL1 than the therapy level TL2 associated with newly-assumed posture state PS2. Therefore, a user-initiated increase from therapy level TL2 may indicate that patient 12 would like to receive the therapy associated with the previous posture state PS1 for longer. Processor 80 may determine whether therapy level TL3 associated with the user-initiated therapy adjustment received following dwell time DT1 is higher than therapy level TL2 associated with posture state PS2. Processor 80 may also determine whether the therapy level TL3 associated with the user-initiated therapy adjustment received following dwell time DT1 is closer to therapy level TL1 associated with the previous posture state PS1 than therapy level TL2 associated with the newly-assumed posture state PS2.

If therapy level TL3 associated with the user-initiated therapy adjustment received following expiration of dwell time DT1 is higher than therapy level TL2 associated with posture state PS2, processor 80 may determine that the therapy adjustment received following dwell time DT1 is consistent with returning toward therapy level TL1 associated with previous posture state PS1. In some examples, processor 80 may also compare the therapy level TL3 associated with the user-initiated change in therapy to therapy level TL1 associated with previous posture state PS1 to determine how closely the user-initiated therapy change matches the therapy level TL1 associated with the previous posture state PS1.

If therapy level TL3 associated with the user-initiated therapy adjustment received following dwell time DT1 was lower than therapy level TL2 associated with posture state PS2, processor 80 may determine that the therapy adjustment received following dwell time DT1 is inconsistent with returning toward therapy level TL1 associated with previous posture state PS1. As a result, processor 80 may determine that the therapy adjustment received following dwell time DT1 does not indicate that a longer dwell time DT1 is preferred. Processor 80 may also determine that the therapy adjustment received following dwell time DT1 does not indicate that a longer dwell time DT1 is preferred if therapy level TL3 associated with the user-initiated therapy adjustment received following dwell time DT1 is closer to therapy level TL2 associated with the newly-assumed posture state PS2 than the therapy level TL1 associated with the previous posture state PS1.

If processor 80 determines that the user-initiated therapy adjustment is an indication that a longer dwell time DT1 is preferred, processor 80 may increase dwell time DT1. For example, processor 80 may set dwell time DT1 to a time longer than the time between time T1 when patient 12 transitioned from posture state PS1 to posture state PS2 and time T3 when a user-initiated therapy adjustment returning the therapy close to or toward therapy level TL1 associated with previous posture state PS1 occurred.

In some examples, a second user-initiated therapy change may indicate when patient 12 would like to receive the therapy associated with the newly-detected posture state PS2. For example, patient 12 or another user may adjust the therapy towards therapy level TL2 associated with posture state PS2 at time T4. As described previously, therapy level TL1 associated with posture state PS1 is higher than therapy level TL2 associated with posture state PS2. A user-initiated therapy adjustment that decreases therapy from a higher therapy level TL3 to a lower therapy level TL4 may be consistent with the therapy adjustment from therapy level TL1 to therapy level TL2 that automatically occurs when patient 12 transitions from posture state PS1 to posture state PS2. Processor 80 may also compare therapy level TL4 associated with the second user-initiated therapy adjustment with therapy level TL2 associated with posture state PS2 to determine how closely therapy level TL4 matches therapy level TL2, e.g., whether therapy TL4 associated with the second user-initiated therapy adjustment is closer to therapy level TL2 associated with newly-assumed posture state PS2 to therapy level TL1 associated with previous posture state PS1. Processor 80 may increase dwell time DT1 based on time T4 associated with the second therapy adjustment. For example, processor 80 may set dwell time DT1 equal to the time between time T1 associated with the transition from posture state PS1 to posture state PS2 and time T4 associated with the second user-initiated therapy adjustment.

Figure 13:
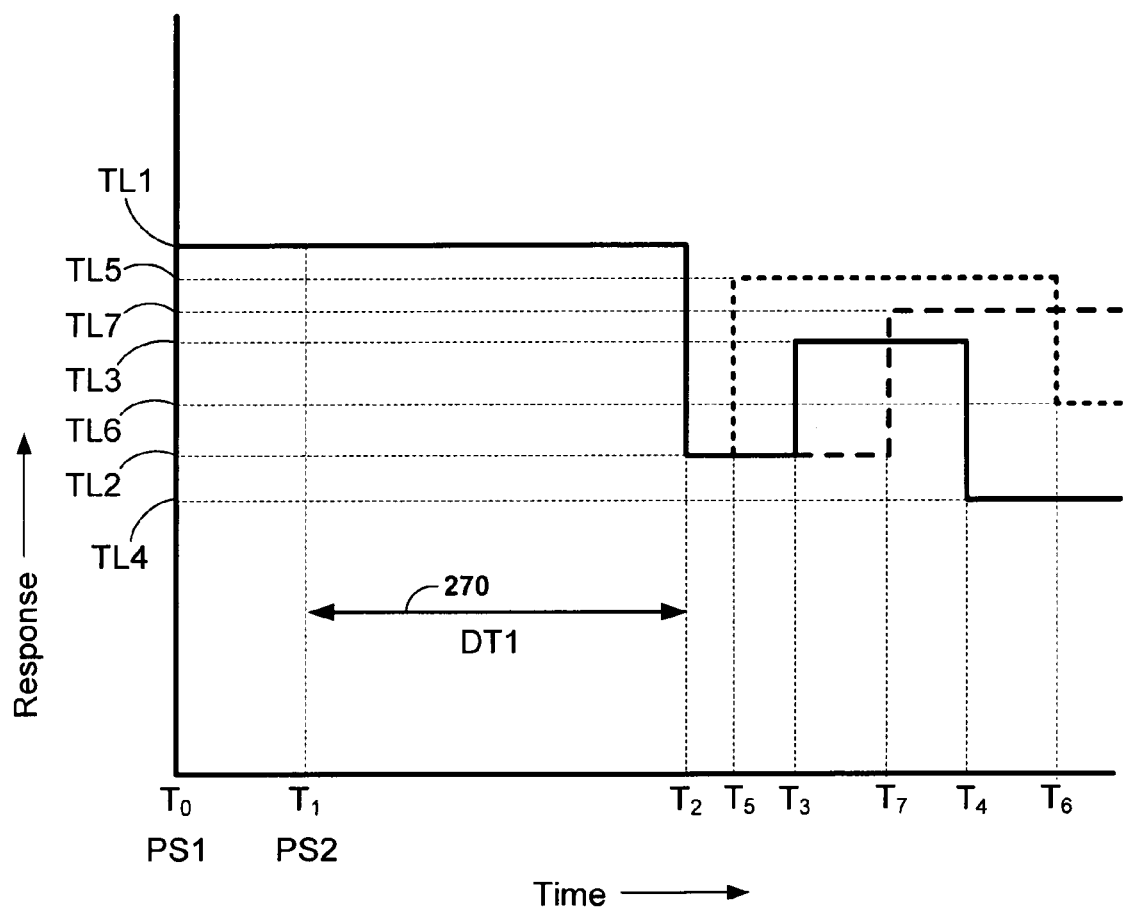
FIG. 13 is an example timing diagram illustrating a composite of user-initiated therapy adjustments recorded following various occurrences of the dwell time.

Processor 80 may also monitor and record user-initiated therapy adjustments each time a dwell time is initiated in response to a posture state transition. FIG. 13 is an example timing diagram illustrating a composite of user-initiated therapy adjustments recorded following various occurrences of dwell time DT1. As previously described, many possibilities exist for selecting which dwell time will be used in a given situation. In the example of FIG. 13, dwell time DT1 may be specific to the particular posture state change that is occurring, i.e., the transition from posture state PS1 to posture state PS2. Although other techniques for selecting dwell time DT1 are also contemplated.

FIG. 13 is substantially similar to FIG. 12 but includes additional user-initiated therapy adjustments that occurred following other occurrences of dwell time DT1, i.e., after patient 12 transitioned from posture state PS1 to posture state PS2. As previously described, dwell time DT1 is initiated at time T1 in response to patient 12 transitioning from posture state PS1 to posture state PS2. Dwell time DT1 expires at time T2. Since, in the example illustrated in FIG. 13, patient 12 did not transition from posture state PS2 during dwell time DT1, therapy delivery according to therapy level TL2 associated with posture state PS2 is initiated at time T2.

At times T3, T5, and T7, user-initiated therapy adjustments occurred. As illustrated in FIG. 13, each of therapy levels TL3, TL5, and TL7 corresponding to times T3, T5, and T7, respectively, are higher than therapy level TL2. Therefore, each of these recorded therapy adjustments may be consistent with returning toward therapy level TL1 associated with previous posture state PS1. Each of times T3, T5, and T7 and corresponding therapy levels TL3, TL5, and TL7 may indicate that patient 12 would prefer a longer dwell time DT1. In other examples, processor 80 may examine how closely the adjusted therapy levels TL3, TL5, and TL7 match therapy level TL1 associated with previous posture state PS1, e.g., whether each of therapy levels TL3, TL5, and TL7 is closer to therapy level TL1 associated with previous posture state PS1 or therapy level TL2 associated with newly-assumed posture state PS2, to determine whether each of the recorded therapy adjustments indicates that patient 12 would prefer a longer dwell time DT1.

Processor 80 may determine a new increased value for dwell time DT1 based on times T3, T5, and T7 that user-initiated therapy adjustments occurred. As one example, processor 80 may set dwell time DT1 to a time longer than the time between time T1 when patient 12 transitioned from posture state PS1 to posture state PS2 and time T7 when the last, i.e., farthest from time T1, of the user-initiated therapy adjustments returning the therapy close to or toward therapy level TL1 associated with previous posture state PS1 occurred.

Additionally, a second user-initiated therapy change may indicate when patient 12 would like to receive the therapy associated with the newly-detected posture state PS2. As previously described, patient 12 or another user may adjust the therapy close to or towards therapy level TL2 associated with posture state PS2 at time T4. Time T6 may indicate another user-initiated therapy adjustment indicating when patient 12 would like to receive the therapy associated with the newly-detected posture state PS2. The user-initiated therapy adjustment occurring at time T6 decreases therapy from a higher therapy level TL5 to a lower therapy level TL6, which may be consistent with the therapy adjustment from therapy level TL1 to therapy level TL2 that automatically occurs when patient 12 transitions from posture state PS1 to posture state PS2. Processor 80 may also determine how closely therapy level TL6 matches therapy level TL2 associated with the newly-assumed posture state PS2, e.g., whether therapy level TL6 is closer to therapy level TL2 associated with the newly-assumed posture state PS2 or therapy level TL1 associated with the previous posture state PS1, to determine whether the user-initiated therapy adjustment occurring at time T6 is consistent with the therapy adjustment from therapy level TL1 to therapy level TL2 that automatically occurs when patient 12 transitions from posture state PS1 to posture state PS2. Processor 80 may increase dwell time DT1 based on times T4 and T6. For example, processor 80 may average times T4 and T6 to obtain an end time and set dwell time DT1 to the time between T1 and the average of times T4 and T6.

In the example of FIG. 13, posture state PS1 is associated with therapy level TL1 and posture state PS2 is associated with therapy level TL2 throughout each occurrence of the posture state transition from posture state PS1 to posture state PS2. In other examples, the therapy levels associated with posture states PS1 and PS2 may change over time, i.e., new therapy levels may be associated with posture states PS1 and PS2.

Figure 14:
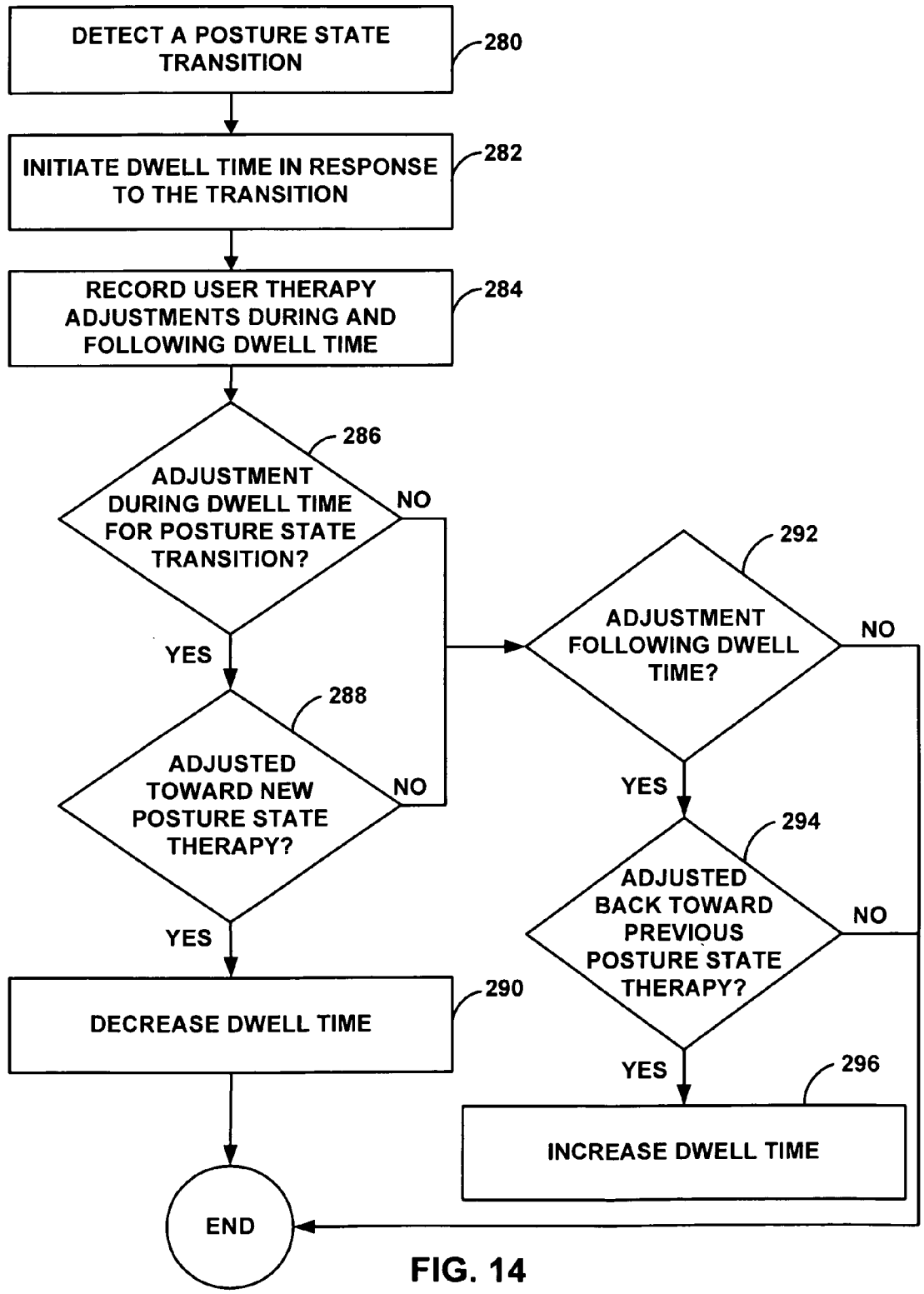
FIG. 14 is a flow diagram illustrating an example method for updating a dwell time based on one or more user-initiated therapy adjustments.

FIG. 14 is a flow diagram illustrating an example method for updating a dwell time based on one or more user-initiated therapy adjustments. Although the description of FIG. 14 primarily refers to IMD 14 and its components (FIG. 4), the method of FIG. 14 is also applicable to other medical devices, such as IMD 26. Also, in some examples, the method of FIG. 14, or portions of the method, may be performed by an external programmer 20, such as patient programmer 30 or clinician programmer 60. Therapy adjustments may be automatic therapy adjustments applied by IMD 14 in response to different detected posture states, and subject to applicable dwell times, or manual therapy adjustments made by a user such as a patient 12 or a clinician.

Adjustments to dwell times may be automatic dwell time adjustments applied by IMD 14 or programmer 20 based on analysis of manual therapy adjustments made during or after dwell times. Alternatively, the dwell time adjustments may be semi-automatic. For example, programmer 20 may present a proposed dwell time adjustment to a user for approval, e.g., via a user interface associated with the programmer. The proposed dwell time adjustment that is presented to the user may be generated automatically by IMD 14 or programmer 20. As a further alternative, a clinician or other user may adjust dwell times via programmer 20 based on analysis of stored therapy adjustment data indicating patient therapy adjustments relative to applicable posture states and dwell times.

In each case, IMD 14 or programmer 20 may store therapy adjustment data for use in evaluating dwell time adjustments. The therapy adjustment data may include a variety of data stored by IMD 14 or programmer 20, such as data that indicates the timing of the therapy adjustments relative to dwell time and detected posture states, the parameters that were adjusted, the parameter values selected by the user (e.g., therapy level), or other pertinent therapy adjustment information. In some cases, in reviewing patient therapy adjustment data, IMD 14 or programmer 20 may require analysis of multiple therapy adjustments in order to adjust the dwell time.

For example, a single patient therapy adjustment within a dwell time of after dwell time expiration may not trigger a dwell time adjustment. However, IMD 14 or programmer 20 may automatically adjust a dwell time to be shorter if N or more patient therapy adjustments are detected within the dwell time, where N is a threshold value triggering dwell time adjustment, and the patient therapy adjustments are consistent with adjustment close to or toward therapy settings, e.g., a therapy level, of the newly detected posture state.

Similarly, IMD 14 or programmer 20 may automatically adjust a dwell time to be longer if N or more patient therapy adjustments are detected after expiration of the dwell time, and the patient therapy adjustments are consistent with adjustment close to or toward therapy settings of a previously detected stable posture. The threshold value N may be the same for all or some dwell times, or different for different dwell times associated with different posture states or posture state transitions. The number of patient therapy adjustments may refer to the number of patient therapy adjustments associated with separate posture state transitions.

For example, IMD 14 and/or programmer 20 may be configured such that N patient therapy adjustments during a single posture state transition does not trigger dwell time adjustment. Rather, at least one patient therapy adjustment in N separate instances of the posture state transition, stable posture state or newly detected posture state may be required to impose a dwell time adjustment for that posture state transition, stable posture state or newly detected posture state.

As an illustration, assuming N=3, if patient 12 enters a therapy adjustment once during the dwell time for a posture state transition from lying back to lying left, IMD 14 and/or programmer 20 does not adjust the dwell time. Similarly, if patient 12 enters four therapy adjustments during the dwell time for a single posture state transition from lying back to lying left, IMD 14 and/or programmer 20 does not adjust the dwell time. However, if IMD 14 and/or programmer 20 determines that patient 12 has entered a therapy adjustment in each of four different instances of the same posture state transition, e.g., lying back to lying left, IMD 14 and/or programmer 20 proceeds to adjust the dwell time.

Requiring a minimum number of therapy adjustments in a minimum number of instances of a posture state transition may have a damping effect on the control loop so that dwell time is not immediately and repeatedly adjusted in response to a single therapy adjustment or a few therapy adjustments for a given posture state. Different or similar threshold values N may be used for different dwell times and posture state transitions. As mentioned above, the actual dwell time adjustment made by IMD 14 and/or programmer 20 may be administered in a variety of different ways.

If at least N therapy adjustments are detected during the dwell time or after the dwell time for a minimum number of instances of a particular posture state transition, the dwell time for that posture state transition may be adjusted based on the timing of the therapy adjustments. If a dwell time is shortened, it may be shortened to a length that extends from the start of the dwell time to the time of the earliest therapy adjustment. Alternatively, the dwell time may be shortened to a length that extends from the start of the dwell time to an average time of the multiple therapy adjustments. If a dwell time is lengthened, it may be increased to a length that extends from the start of the dwell time to the time of the latest therapy patient adjustment. Alternatively, the dwell time may be increased to a length that extends from the start of the dwell time to an average time of the multiple patient therapy adjustments.

In some cases, IMD 14 and/or programmer 20 may maintain one or more counters that track the number of patient therapy adjustments for multiple instances of the different posture transitions, and increase or reduce dwell times based on comparison of the counter values to applicable threshold values for pertinent posture state transitions. If the number of patient therapy adjustments during or after dwell time exceeds the threshold number, IMD 14 and/or programmer 20 automatically adjusts the dwell time, e.g., as described above. As a further example, in some cases, IMD 14 and/or programmer 20 may adjust the dwell time in fixed increments, progressively increasing or decreasing the dwell time, as applicable, based on the number of patient therapy adjustments indicated by the counter value, or calculating an amount of increase or decrease as a function of the counter value.

In the example of FIG. 14, posture state module 86, e.g., in conjunction with processor 80, may detect a posture state transition (280). In response to the detected posture state transition, dwell time module 89 may initiate a dwell time (282). Processor 80 may record user-initiated therapy adjustments during and following the dwell time (284). User-initiated therapy adjustments occurring during or following the dwell time may indicate that patient 12 would prefer a shorter or longer dwell time.

Processor 80 may identify whether a user-initiated therapy adjustment occurred during the dwell time (286). If a user-initiated therapy adjustment occurred during the dwell time, processor 80 may determine whether the user-initiated therapy adjustment is consistent with transitioning close to or toward a therapy associated with the new posture state that patient 12 recently transitioned into (288). A therapy adjustment close to or toward the therapy associated with the new posture state may indicate that patient 12 would prefer to receive the therapy associated with the new posture state at an earlier time. For example, a therapy adjustment close to or toward a therapy associated with a new posture state may be a therapy adjustment that changes an amplitude level close to or toward an amplitude level of the therapy associated with the new posture state. In response to determination 286 and 288, processor 80 may decrease the dwell time, e.g., the dwell time associated with the specific posture state transition, if the user-initiated therapy adjustment is consistent with transitioning close to or toward a therapy associated with the new posture state (290). Although FIG. 14 illustrates decreasing dwell time (290) in response to a single therapy adjustment during the dwell time for a posture state transition (286), as described above, decreasing dwell time may require patient adjustments in multiple instances of the posture state transition, i.e., a threshold number N of patient adjustments.

If a user-initiated therapy adjustment did not occur during the dwell time (286) or the user-initiated therapy adjustment that occurred during the dwell time is not consistent with transitioning close to or toward a therapy associated with the new posture state (288), processor 80 may determine whether a therapy adjustment occurred following the dwell time (292). If a user-initiated therapy adjustment did occur following the dwell time, processor 80 may determine whether the user-initiated therapy adjustment is consistent with transitioning back close to or toward the therapy associated with the previous posture state that patient 12 recently transitioned from (294). A user-initiated therapy adjustment that transitions therapy delivery back close to or toward the therapy associated with the previous posture state may indicate that patient 12 would prefer a longer dwell time. Therefore, if the user-initiated therapy adjustment is consistent with a transition back close to or toward the therapy associated with the previous posture state, processor 80 may decrease the dwell time, e.g., the dwell time associated with the specific posture state transition (296). Dwell time module 89 and/or memory 82 may store the updated dwell time value for use in delivery of posture-responsive therapy for subsequent posture state transitions by patient 12.

Figure 15:
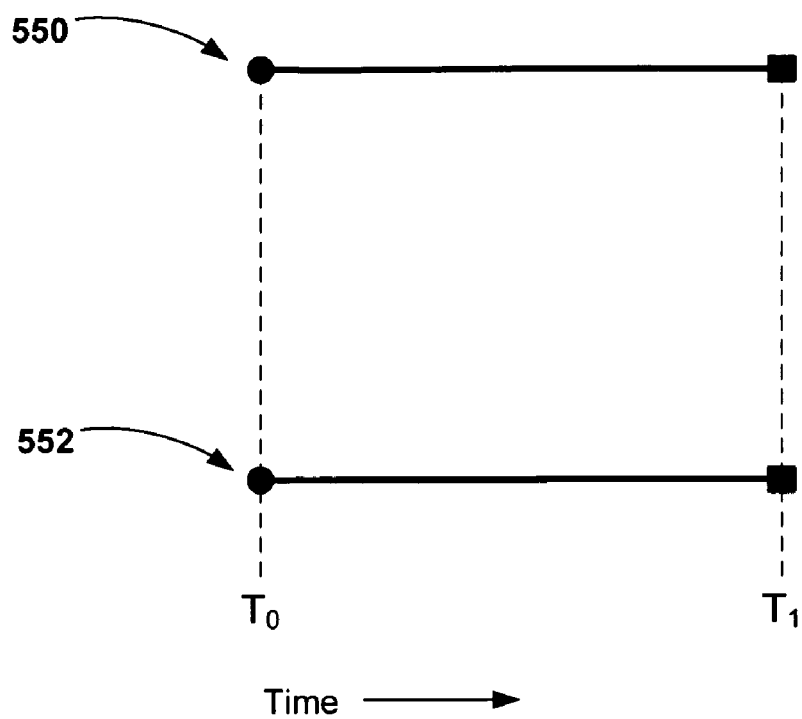
FIG. 15 is a conceptual diagram illustrating an example posture search timer and posture stability timer when a patient remains in one posture state.

FIGS. 15-19 illustrate examples of the application of a search timer and stability timer to associate patient therapy adjustments with posture states. If a patient therapy adjustment is associated with a posture state, it may be used to evaluate whether a dwell time for the posture state should be adjusted. FIG. 15 is a conceptual diagram illustrating example posture search timer 550 and posture stability timer 552 when patient 12 remains in one posture state. In some examples, IMD 14 must be able to correctly associate each therapy adjustment with a therapy parameter to the intended posture state of patient 12 when the therapy adjustment was made. For example, patient 12 may make therapy adjustments to customize the therapy either after patient 12 moves to a different posture state or in anticipation of the next posture state. IMD 14 may employ posture search timer 550 and posture stability timer 552 to track therapy adjustments and the current posture state of patient 12. Although IMD 14 may associate therapy adjustments of any therapy parameter to a posture state, some examples of IMD 14 may only allow the association of amplitude changes. In this manner, patient 12 may change different therapy parameters such as pulse width, pulse rate, or electrode configuration, but IMD 14 will not store these therapy adjustments as being associated to any posture state in some examples.

Posture search timer 550 has a search period that is a set amount of time that patient 12 has from the time the therapy adjustment is made, when posture search timer 550 starts, to when the final posture state must begin, prior to the expiration of the search period. In other words, in this example, the patient therapy adjustment will not be associated with a posture state entered after the search period has expired. In addition, posture stability timer 552 has a stability period that is a set amount of time that patient 12 must remain within the final posture state for the therapy adjustment made to be associated with the final posture state. Posture stability timer 552 restarts at any time that patient 12 changes posture states. In order to associate a therapy adjustment with a posture state, the stability timer for the posture state must start before the end of the search period, and the posture state must not change during the stability period. Therefore, the search period and stability period must overlap for the therapy adjustment to be associated with a posture state not currently occupied by patient 12 when the therapy adjustment was made.

In the example of FIG. 15, patient 12 made a therapy adjustment to one of the therapy parameters, such as voltage or current amplitude, at time $T_0$. Therefore, posture search timer 550 starts at $T_0$ and runs for a predetermined search period until time $T_1$. When the therapy adjustment is made, posture stability timer 552 also starts at time $T_0$ in the current posture state of patient 12 and runs for the stability period. In the example of FIG. 15, the stability period is the same as the search period. Since patient 12 has not changed to any different posture states between times $T_0$ and $T_1$, the stability period also ends at $T_1$. The therapy adjustment made by patient 12 at time $T_0$ is associated with the posture state sensed between times $T_0$ and $T_1$ because both the search period and stability period overlap. In the example of FIG. 15, posture search timer 550 and posture stability timer 552 may not be needed, but their purpose in some example implementations may become clearer in the following examples.

The search period of posture search timer 550 may be of any time duration desired by a device manufacturer, and the clinician may or may not be permitted to set the search period to a desired value or within a predetermined search range. Generally, the search period may be between approximately 30 seconds and 30 minutes, but it may be set to any time desired, including a time that is outside of that range. More specifically, the search period may be between approximately 30 seconds and 5 minutes, or more preferably 2 minutes to 4 minutes in order to provide a reasonable amount of time for patient 12 to be situated in the final desired posture state. In some examples, and as described in the examples of FIGS. 15-19, the search period is approximately 3 minutes. In other cases, shorter search periods may be used, e.g., approximately 1 second to 60 seconds, or approximately 5 seconds to 20 seconds.

In addition, the stability period of posture stability timer 552 may be of any time duration desired by the manufacturer or clinician, where the clinician may or may not be permitted to set the stability period. Generally, the stability period is between approximately 30 seconds and 30 minutes, but it may be set to any time desired, including times outside of that range. More specifically, the stability period may be between approximately 30 seconds and 5 minutes, and more preferably 2 minutes to 4 minutes, in order to ensure that patient 12 is situated in the final desired posture state for a reasonable amount of time and that the final posture state is not just some transitional or interim posture state. In some examples, and as described in the examples of FIGS. 15-19, the stability period is approximately 3 minutes. Although the search period and stability period may have the same duration, they may be different in other examples. In other cases, shorter stability periods may be used, e.g., approximately 1 second to 60 seconds, or approximately 5 seconds to 20 seconds.

As described herein, associating therapy adjustments with intended posture states may allow a processor to review therapy adjustments made by patient 12 while assuming, or transitioning to, each posture state. These adjustments may be used to determine whether to modify a dwell time, e.g., decrease a dwell time for a specified posture state transition.

Figure 16:
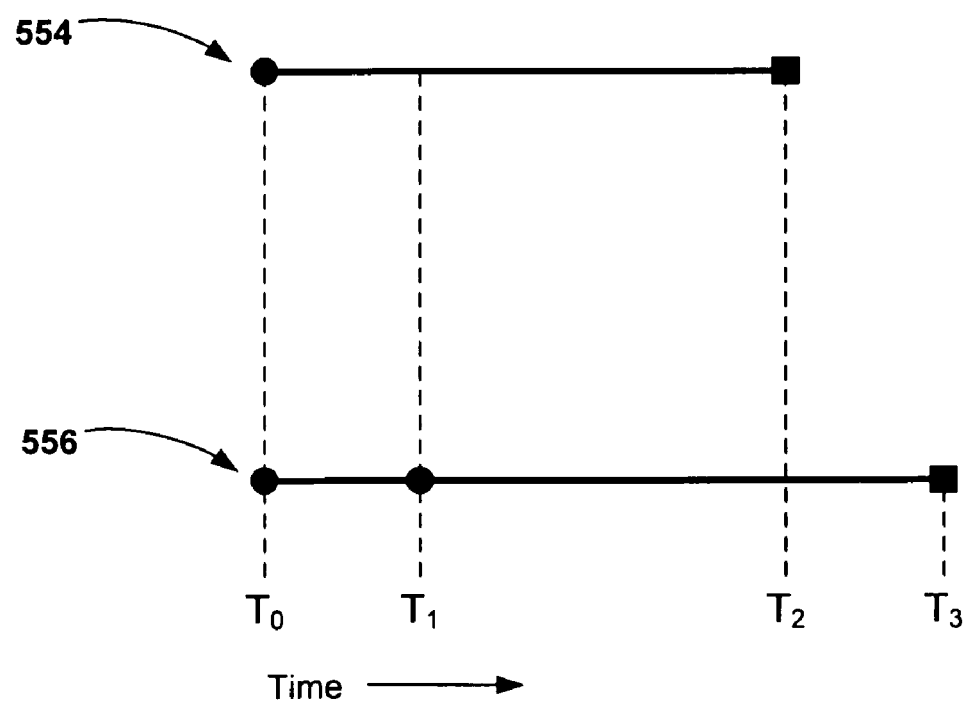
FIG. 16 is a conceptual diagram illustrating an example posture search timer and posture stability timer with one change in posture state.

FIG. 16 is a conceptual diagram illustrating example posture search timer 554 and posture stability timer 556 with one change in posture state. As shown in FIG. 16, patient 12 makes an anticipatory therapy adjustment for the next posture state that patient 12 does not currently occupy. In other words, patient 12 makes a therapy adjustment that the patient may believe is desirable for a given posture in anticipation of transitioning to that posture on an imminent or near-term basis. Posture search timer 554 and posture stability timer 556 start at time $T_0$ when patient 12 makes a therapy adjustment in a current posture state occupied at time $T_0$. At time $T_1$, patient 12 changes to a second posture state that is different than the initial posture state occupied at time $T_0$. Therefore, posture stability timer 556 restarts at time $T_1$, with the change to the new posture state, still within the search duration of posture search timer 554.

In some implementations, patient therapy adjustments received during the search period restart the search period. As a result, a series of patient therapy adjustments that are entered closely in time are, in effect, clustered together such that intermediate adjustments are not counted for the posture state. Instead, the last adjustment in a series of closely spaced (in time) adjustments is associated with the posture state to represent the final adjustment that brought the parameter to a level or value deemed appropriate by the patient 12 for the given posture state. If the search period is three minutes, for example, and the patient 12 makes four adjustments in voltage amplitude within three minutes of one another, e.g., 4.6 volts to 4.8 volts, 4.8 volts to 5.0 volts, 5.0 volts to 5.1 volts, 5.1 volts to 5.3 volts, then the final adjustment value of 5.3 volts may be associated with the posture state.

Each time a new adjustment is entered within the search period, the search period is reset. Once the final adjustment is made, however, if there are no further adjustments for another three minutes, and the stability period is satisfied for the detected posture state, then the final adjustment is associated with the posture state. Clustering of a number of patient therapy adjustments can be useful in order to present a series of closely timed adjustments as a single programming intervention event. Treatment of clustered adjustments as a single programming intervention event may be especially appropriate if the values of the adjustments are also close to one another.

Time $T_2$ indicates the end of posture search timer 554. Consequently, the only posture state that processor 80 of IMD 14 will associate with the therapy adjustment is the second posture state as long as the second posture state satisfies the stability period of posture stability timer 556, i.e., the patient occupies the second posture state for the stability period. At time $T_3$, patient 12 is still in the second posture when the stability period ends, and the therapy adjustment is associated then to the second posture state because the stability period overlapped with the search period.

It should be noted that patient 12 may make additional therapy adjustments within the search period. If this occurs, any previous therapy adjustments made before the search period or stability period is completed are not associated to any posture state. Therefore, both the search period and stability period must lapse, i.e., expire, in order for a therapy adjustment to be associated with a posture state. However, in some examples, IMD 14 may allow therapy adjustments to be associated with posture states as long as the search period has lapsed or no different posture state was sensed during the search period.

Figure 17:
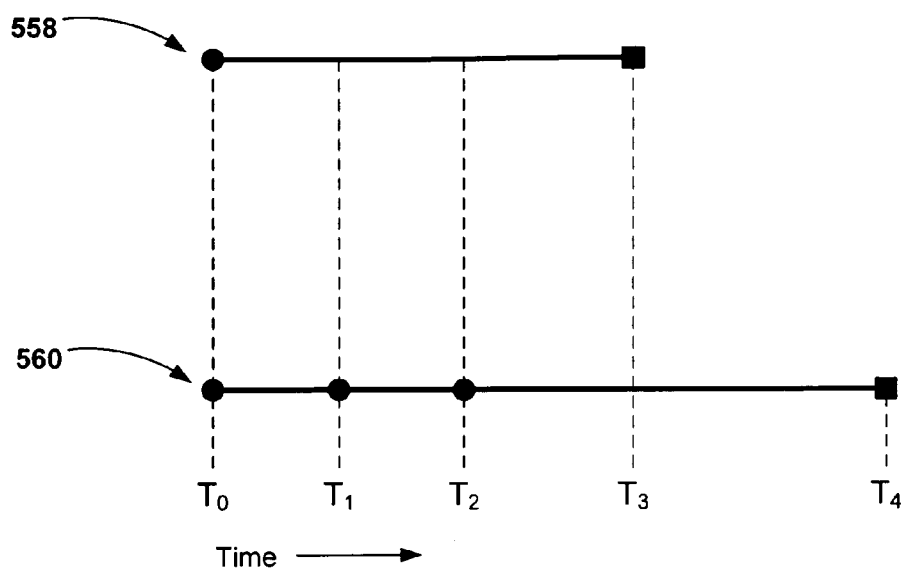
FIG. 17 is a conceptual diagram illustrating an example posture search timer and posture stability timer with two changes in posture states.

FIG. 17 is a conceptual diagram illustrating example posture search timer 550 and posture stability timer 560 with two changes in posture states. As shown in FIG. 17, patient 12 makes an anticipatory therapy adjustment but is engaged in an interim posture state before settling into the final posture state. Posture search timer 558 and posture stability timer 560 both start at time $T_0$ when patient 12 makes a therapy adjustment in a current posture state engaged at time $T_0$.

At time $T_1$, patient 12 changes to a second posture state, or an interim posture state, that is different than the initial posture state engaged at time $T_0$. Therefore, posture stability timer 560 restarts at time $T_1$, still within the search duration of posture search timer 558. At time $T_2$, patient 12 changes to a third posture state, and again posture stability timer 560 restarts. Time $T_3$ indicates the end of posture search timer 558, so the only posture state that processor 80 of IMD 14 will associate with the therapy adjustment is the third posture state begun at time $T_2$ as long as the third posture state satisfies the stability period of posture stability timer 560. At time $T_4$, patient 12 is still in the third posture when the stability period ends, and the therapy adjustment is associated then to the third and final posture state because the stability period of the third posture state overlapped with the search period.

Figure 18:
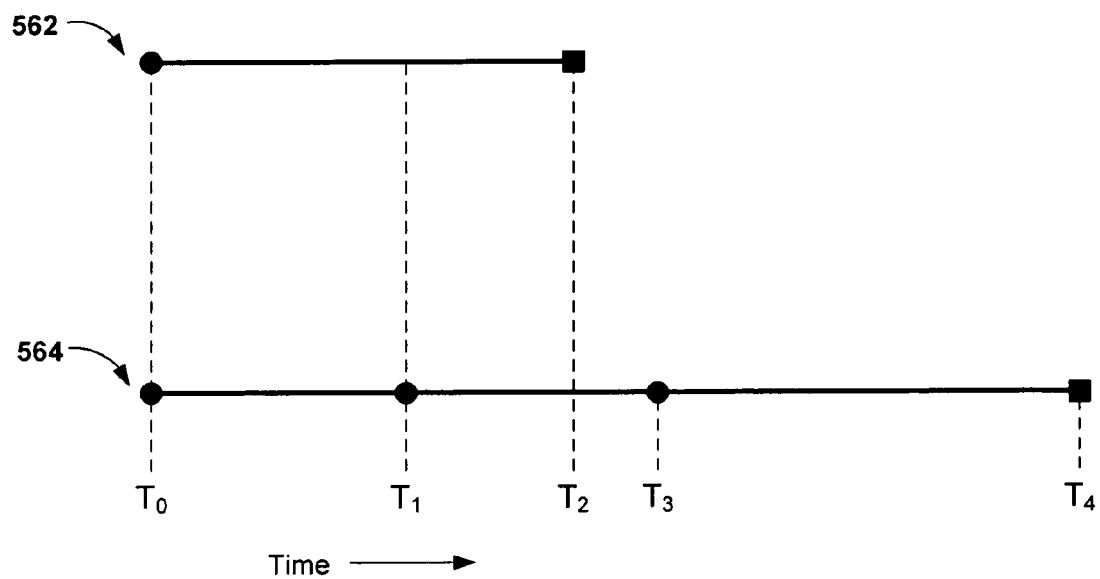
FIG. 18 is a conceptual diagram illustrating an example search timer and posture stability timer with the last posture state change occurring outside of the posture search timer.

FIG. 18 is a conceptual diagram illustrating example search timer 562 and posture stability timer 564 with the last posture state change occurring outside of the posture search timer. As shown in FIG. 18, patient 12 makes an anticipatory therapy adjustment but is engaged in an interim posture state too long before settling into the final posture state for the therapy adjustment to be associated with any posture state. Posture search timer 562 and posture stability timer 564 both start at time $T_0$ when patient 12 makes a therapy adjustment in a current posture state engaged at time $T_0$. At time $T_1$, patient 12 changes to a second posture state, or an interim posture state, that is different than the initial posture state engaged at time $T_0$. Therefore, posture stability timer 564 restarts at time $T_1$, still within the search duration of posture search timer 562.

However, the search timer expires at time $T_2$, before patient 12 changes to a third posture state at time $T_3$, when posture stability timer 564 again restarts. The stability period for the third posture state then expires at time $T_4$. Since the third posture state did not start before the search period expired at time $T_2$, the search period and stability period do not overlap and the therapy adjustment from time $T_0$ is not associated to any posture state. In other examples, therapy adjustments may still be associated with the posture state occupied at time $T_0$ when the search period and last stability period do not overlap.

The following is a further illustration of the example described in FIG. 18 to put the example in the context of an example patient scenario. Patient 12 may be engaged in the upright posture state when patient 12 makes the therapy adjustment at time $T_0$. In this example, the search duration is three minutes and the stability duration is also three minutes. After two minutes, or at time $T_1$, patient 12 transitions to the lying left posture to cause processor 80 of IMD 14 to restart posture stability timer 560.

If patient 12 remains within the lying left posture for the full three minutes of the stability duration, then the therapy adjustment would be associated with the lying left posture. However, patient 12 leaves the lying left posture after only two minutes, or at time $T_3$, outside of the search duration. At this point the therapy amplitude made at time $T_0$, will not be associated for the next posture state of patient 12. Therefore, the next posture state may be the lying back posture state. Once IMD 14 senses the lying back posture state, IMD 14 may change therapy according to the therapy parameters associated with the lying back posture because IMD 14 is operating in the automatic posture state-responsive mode. No new associations with the therapy adjustment would be made in the example of FIG. 18.

Figure 19:
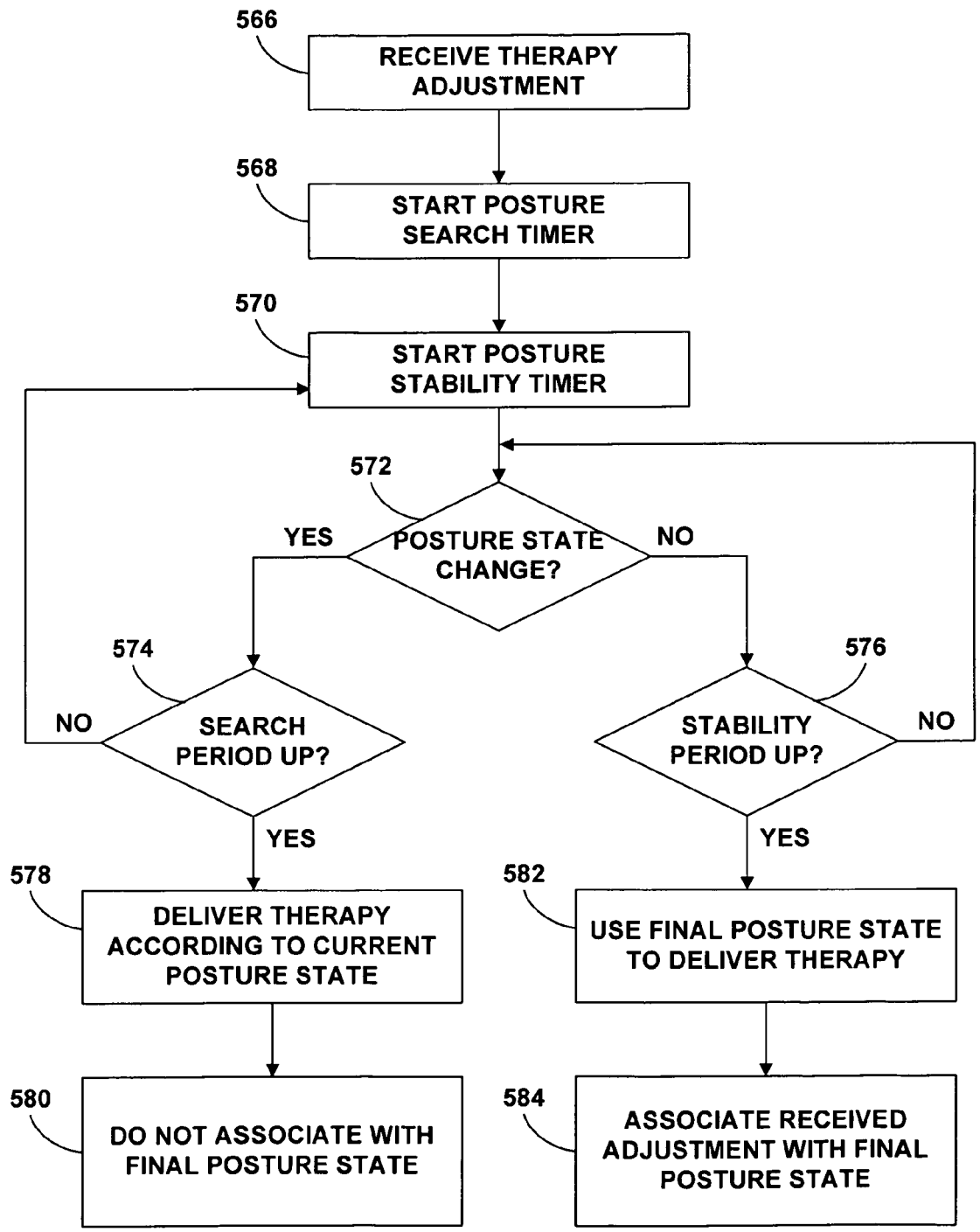
FIG. 19 is a flow diagram illustrating an example method for associating a received therapy adjustment with a posture state to evaluate dwell time adjustment.

FIG. 19 is a flow diagram illustrating an example method for associating a received therapy adjustment with a posture state. Although the example of FIG. 17 will be described with respect to patient programmer 30 and IMD 14, the technique may be employed in any external programmer 20 and IMD or other computing device. As shown in FIG. 17, user interface 106 receives the therapy adjustment from patient 12 (566) and processor 80 of IMD 14 immediately starts the posture search timer (568) and the posture stability timer (570).

If the posture state of patient 12 does not change (572), processor 80 checks to determine if the stability period has expired (576). If the stability period has not expired (576), processor 80 continues to sense for a posture state change (572). If the stability period has expired (576), processor 80 uses the final posture state, i.e., the currently sensed posture state, to select therapy parameters to deliver therapy (582). Processor 80 then associates the therapy adjustment with the final posture state and counts the therapy adjustment for that posture state (584).

If processor 80 senses a posture state change (572), processor 80 determines if the search period has expired (574). If the search period has not expired (574), then processor 80 restarts the posture stability timer (570). If the search period has expired (574), then processor 80 automatically delivers posture state-responsive therapy to patient 12 according to the current posture state (578). Processor 80 does not associate the patient therapy adjustment with the final posture state because the search period did not overlap with the stability period (580).

In some examples, as an alternative, a posture stability timer may be employed without the use of a posture search timer. As described with respect to posture stability timer 560, the posture stability timer may be started after a therapy adjustment and reset each time patient 12 changes posture states prior to expiration of the posture stability timer. When the posture stability timer 560 expires, the therapy adjustment may be associated with the posture state that patient 12 is occupying at that time. In this manner, the therapy adjustment may be associated with the first stable posture state, i.e., the first posture state that remains stable for the duration of the posture stability timer, after the therapy adjustment, regardless of the amount of time that has past since the therapy adjustment. Hence, in some implementations, processor 80 may apply only a stability timer without a search timer.

As described with respect to FIGS. 15-19, patient 12 may make an anticipatory therapy adjustment intended for posture state in anticipation of transitioning to that posture state on an imminent or near-term basis. Although the therapy adjustment occurs before patient 12 actually transitions to the new posture state for which the therapy adjustment is intended, the therapy adjustment may be associated with the new, intended posture state upon expiration of the posture search and stability timers. As described with respect to the examples of FIGS. 16 and 17, the therapy adjustment may be associated with the new, intended posture state if the search period does not expire prior to entering the new, intended posture state and the posture stability requirement is satisfied for the new, intended posture state. In some examples, anticipatory therapy adjustments may also be used to update dwell time values.

Using association logic based on a search timer and/or stability timer as described in this disclosure, a processor can detect a patient therapy adjustment that is associated with a posture state, but is entered and detected before detection of the posture state, and before commencement of the dwell time for the posture state. This type of anticipatory therapy adjustment prior to transitioning to the posture state for which the therapy adjustment is intended and prior to initiating a corresponding dwell time may indicate that patient 12 would prefer a shortened dwell time. For example, a patient-initiated therapy adjustment in anticipation of transitioning to a posture state may indicate that the patient would prefer to receive the therapy associated with that posture state as soon as possible. Shortening the dwell time associated with the posture state or the specific posture state transition that patient 12 undergoes may allow patient 12 to receive the therapy associated with the new posture state sooner.

Processor 80 may decrease the dwell time associated with the new, intended posture state or the specific posture state transition that patient 12 undergoes from a first posture state to the new, intended posture state for subsequent detections of the posture state or posture state transition. In some examples, processor 80 may monitor the number of anticipatory therapy adjustments associated with a posture and/or posture state transition and decrease the dwell time associated with the posture or posture state transition based on the number of anticipatory therapy adjustments associated with the posture or posture state transition, e.g., over multiple occurrences of the posture state transition.

As one example, processor 80 may incrementally decrease the dwell time associated with the posture state or posture state transition. For example, processor 80 may decrease the dwell time by a specified amount, e.g., percentage, each time an anticipatory therapy adjustment is associated with the posture state or posture state transition. As another example, processor 80 may decrease the dwell time after a threshold number of anticipatory therapy adjustments are associated with the posture or posture state transition. As yet another example, processor 80 may set the dwell time for the posture or posture state transition to approximately zero, e.g., after one or a threshold number of anticipatory therapy adjustments are associated with the posture or posture state transition.

In some examples, processor 80 may also examine whether the anticipatory therapy adjustment received prior to transitioning to the new, intended posture state and initiating a corresponding dwell time is consistent with transitioning close to or toward a therapy associated with the new, intended posture state, as described in further detail with respect to FIGS. 10-14. In some examples, the posture search and stability timers described with respect to FIGS. 15-19 may be used to associate therapy adjustments received during and after the dwell time with the appropriate posture state, e.g., in addition to associating anticipatory therapy adjustments received prior to the dwell time with the intended posture state.

Various aspects of the techniques described in this disclosure may be implemented within an IMD, an external programmer, or a combination of both. Moreover, in some aspects, information may be processed by the IMD, programmer or a dedicated processing device such as a network server. For example, posture state information may be stored in raw form in an IMD and retrieved from the IMD by an external programmer or other external device for evaluation of dwell time adjustments. Alternatively, the IMD may process the posture state information at least partially for retrieval by an external device. An IMD or programmer may be configured to adjust dwell time automatically or semi-automatically. The particular implementations described in this disclosure are presented for purposes of illustration and without limitation as to the techniques broadly described in this disclosure.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

In addition, it should be noted that the systems described herein may not be limited to treatment of a human patient. In alternative embodiments, these systems may be implemented in non-human patients, e.g., primates, canines, equines, pigs, and felines. These animals may undergo clinical or research therapies that my benefit from the subject matter of this disclosure.

Many examples of the disclosure have been described. Various modifications may be made without departing from the scope of the claims. These and other examples are within the scope of the following claims.

The invention claimed is:

1. A method comprising:
    delivering therapy to a patient;
    detecting a posture state transition of a patient;
    after a time delay following the posture state transition, adjusting the therapy based on the posture state transition;
    detecting a patient adjustment of the therapy; and
    adjusting the time delay based on the patient adjustment.

2. The method of claim 1, wherein adjusting the time delay comprises adjusting the time delay if the patient adjustment is detected during or after the time delay.

3. The method of claim 1, wherein adjusting the time delay comprises adjusting the time delay if the patient adjustment is detected during the time delay.

4. The method of claim 1, wherein adjusting the time delay comprises adjusting the time delay if a number of patient adjustments detected during multiple instances of the posture state transition exceeds a threshold.

5. The method of claim 1, wherein adjusting the time delay comprises reducing the time delay if the patient adjustment is detected during the time delay.

6. The method of claim 5, wherein reducing the time delay comprises reducing the time delay based on timing of the patient adjustment.

7. The method of claim 1, wherein adjusting the time delay comprises increasing the time delay if the patient adjustment is detected after the time delay.

8. The method of claim 7, wherein increasing the time delay comprises increasing the time delay based on timing of the patient adjustment.

9. The method of claim 1, further comprising determining whether the patient adjustment is consistent with the adjustment of therapy based on the posture state transition, wherein adjusting the time delay comprises adjusting the time delay based on the patient adjustment and the determination of whether the patient adjustment is consistent with the adjustment of therapy based on the posture state transition.

10. The method of claim 1, wherein the posture state transition comprises a transition from a first posture state to a second posture state, and wherein each of the first and second posture states comprises at least one of a posture or a combination of a posture and an activity level.

11. The method of claim 1, further comprising adjusting the therapy based on a plurality of different posture state transitions after time delays following the respective posture state transitions, wherein at least some of the time delays are different for different posture state transitions.

12. The method of claim 11, wherein adjusting the time delay comprises adjusting different time delays for different posture state transitions based on patient adjustments associated with the respective time delays.

13. The method of claim 1, wherein delivering the therapy to the patient comprises delivering the therapy to the patient from an implantable medical device, wherein the therapy comprises electrical stimulation therapy.

14. A medical device comprising:
    a posture state module that detects a posture state transition of a patient;
    a therapy module that delivers therapy to a patient; and
    a processor that, after a time delay following the posture state transition, adjusts the therapy based on the posture state transition, detects a patient adjustment of the therapy, and adjusts the time delay based on patient adjustment.

15. The medical device of claim 14, wherein the processor adjusts the time delay if the patient adjustment is detected during or after the time delay.

16. The medical device of claim 14, wherein the processor adjusts the time delay if the patient adjustment is detected during the time delay.

17. The medical device of claim 14, wherein the processor adjusts the time delay if a number of patient adjustments detected during multiple instances of the posture state transition exceeds a threshold.

18. The medical device of claim 14, wherein the processor reduces the time delay if the patient adjustment is detected during the time delay.

19. The medical device of claim 18, wherein the processor reduces the time delay based on timing of the patient adjustment.

20. The medical device of claim 14, wherein the processor increases the time delay if the patient adjustment is detected after the time delay.

21. The medical device of claim 20, wherein the processor increases the time delay based on timing of the patient adjustment.

22. The medical device of claim 14, wherein the processor determines whether the patient adjustment is consistent with the adjustment of therapy based on the posture state transition, and adjusts the time delay based on patient adjustment and the determination of whether the patient adjustment is consistent with the adjustment of therapy based on the posture state transition.

23. The medical device of claim 14, wherein the posture state transition comprises a transition from a first posture state to a second posture state, and wherein each of the first and second posture states comprises at least one of a posture or a combination of a posture and an activity level.

24. The medical device of claim 14, wherein the processor adjusts the therapy based on a plurality of different posture state transitions after time delays for the respective posture state transitions, wherein at least some of the time delays are different for different posture state transitions.

25. The medical device of claim 24, wherein the processor adjusts different time delays for different posture state transitions based on patient adjustments associated with the respective time delays.

26. The medical device of claim 14, wherein the medical device comprises an implantable medical device, and the therapy comprises electrical stimulation therapy.

27. A medical system comprising:
a medical device that detects a posture state transition of a patient, and delivers therapy to a patient after a time delay following the posture state transition;
an external programmer that receives a patient adjustment of the therapy; and
a processor that adjusts the time delay based on the patient adjustment.

28. The medical system of claim 27, wherein the processor adjusts the time delay if the patient adjustment is received during or after the time delay.

29. The medical system of claim 27, wherein the processor adjusts the time delay if the patient adjustment is received during the time delay.

30. The medical system of claim 27, wherein the processor adjusts the time delay if a number of patient adjustments received during multiple instances of the posture state transition exceeds a threshold.

31. The medical system of claim 27, wherein the processor reduces the time delay if the patient adjustment is received during the time delay.

32. The medical system of claim 27, wherein the processor increases the time delay if the patient adjustment is detected after the time delay.

33. The medical system of claim 27, wherein the processor adjusts the therapy based on a plurality of different posture state transitions upon expiration of time delays for the respective posture state transitions, wherein at least some of the time delays are different for different posture state transitions.

34. The medical system of claim 33, wherein the processor adjusts different time delays for different posture state transitions based on patient adjustments associated with the respective time delays.

35. The medical system of claim 27, wherein the medical device comprises an implantable medical device, and the therapy comprises electrical stimulation therapy, the medical system further comprising a telemetry interface that supports communication between the external programmer and the implantable medical device.

36. The medical system of claim 27, wherein the processor resides within the external programmer.

37. The medical system of claim 27, wherein the processor resides within the medical device.

38. A medical device comprising:
means for delivering therapy to a patient;
means for detecting a posture state transition of a patient;
means for, after a time delay following the posture state transition, adjusting the therapy based on the posture state transition;
means for detecting a patient adjustment of the therapy; and
means for adjusting the time delay based on the patient adjustment.

39. The medical device of claim 38, wherein the means for adjusting the time delay comprises means for adjusting the time delay if the patient adjustment is detected during or after the time delay.

40. The medical device of claim 38, wherein the means for adjusting the time delay comprises means for adjusting the time delay if the patient adjustment is detected during the time delay.

41. The medical device of claim 38, wherein the means for adjusting the time delay comprises means for adjusting the time delay if a number of patient adjustments detected during multiple instances of the posture state transition exceeds a threshold.

42. The medical device of claim 38, wherein the means for adjusting the time delay comprises means for reducing the time delay if the patient adjustment is detected during the time delay.

43. The medical device of claim 38, wherein the means for adjusting the time delay comprises means for increasing the time delay if the patient adjustment is detected after the time delay.

44. The medical device of claim 38, further comprising means for adjusting the therapy based on a plurality of different posture state transitions after time delays following the respective posture state transitions, wherein at least some of the time delays are different for different posture state transitions, and wherein the means for adjusting the dwell time comprises means for adjusting different time delays for different posture state transitions based on patient adjustments associated with the respective time delays.

45. The medical device of claim 38, wherein the means for delivering the therapy to the patient comprises means for delivery therapy to the patient from an implantable medical device, wherein the therapy comprises electrical stimulation therapy.

* * * * *